(12) United States Patent
Goldman et al.

(10) Patent No.: US 7,150,989 B2
(45) Date of Patent: Dec. 19, 2006

(54) TELOMERASE IMMORTALIZED NEURAL PROGENITOR CELLS

(75) Inventors: Steven A. Goldman, South Salem, NY (US); Neeta Singh Roy, New York, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 452 days.

(21) Appl. No.: 10/217,252

(22) Filed: Aug. 9, 2002

(65) Prior Publication Data
US 2003/0082812 A1 May 1, 2003

Related U.S. Application Data

(60) Provisional application No. 60/311,626, filed on Aug. 10, 2001.

(51) Int. Cl.
*C12N 5/00* (2006.01)
*C12N 5/08* (2006.01)
*C12N 5/02* (2006.01)
*C12N 15/63* (2006.01)

(52) U.S. Cl. ............ 435/325; 435/368; 435/375; 435/455

(58) Field of Classification Search .......... 435/325, 435/368, 375, 377, 366, 455
See application file for complete search history.

(56) References Cited

U.S. PATENT DOCUMENTS

| | | | |
|---|---|---|---|
| 4,997,929 | A | 3/1991 | Collins et al. |
| 5,082,774 | A | 1/1992 | Heinrich |
| 5,145,774 | A | 9/1992 | Tarnowski et al. |
| 5,169,762 | A | 12/1992 | Gray et al. |
| 5,196,315 | A | 3/1993 | Ronnett et al. |
| 5,217,893 | A | 6/1993 | Ronnett et al. |
| 5,272,063 | A | 12/1993 | Chan et al. |
| 5,308,763 | A | 5/1994 | Ronnett et al. |
| 5,338,839 | A | 8/1994 | McKay et al. |
| 5,491,084 | A | 2/1996 | Chalfie et al. |
| 5,502,176 | A | 3/1996 | Tenen et al. |
| 5,583,016 | A | 12/1996 | Villeponteau et al. |
| 5,639,618 | A | 6/1997 | Gay |
| 5,747,317 | A | 5/1998 | Cao |
| 5,753,505 | A | 5/1998 | Luskin |
| 5,753,506 | A | 5/1998 | Johe |
| 5,830,651 | A * | 11/1998 | Cauley et al. ............ 435/6 |
| 5,874,304 | A | 2/1999 | Zolotukhin et al. |
| 5,917,025 | A | 6/1999 | Collins |
| 5,968,829 | A | 10/1999 | Carpenter |
| 5,972,605 | A | 10/1999 | Villeponteau et al. |
| 6,093,809 | A | 7/2000 | Cech et al. |
| 6,146,826 | A | 11/2000 | Chalfie et al. |
| 6,166,178 | A | 12/2000 | Cech et al. |
| 6,245,564 | B1 | 6/2001 | Goldman et al. |
| 6,261,836 | B1 | 7/2001 | Cech et al. |
| 6,475,789 | B1 | 11/2002 | Cech et al. |

FOREIGN PATENT DOCUMENTS

| | | |
|---|---|---|
| WO | WO 96/38541 | 12/1996 |
| WO | WO 97/07200 | 2/1997 |
| WO | WO 98/32879 | 7/1998 |
| WO | WO 99/29279 | 6/1999 |
| WO | WO 99/49014 | 9/1999 |
| WO | WO 00/23571 | 4/2000 |
| WO | WO 01/46384 | 6/2001 |
| WO | WO 01/53503 | 7/2001 |
| WO | WO 01/68815 | 9/2001 |

OTHER PUBLICATIONS

Bodnar et al., "Extension of Life-Span by Introduction of Telomerase Into Normal Human Cells," *Science*, 279(5349):349-352 (1998).

Klapper et al., "Differential Regulation of Telomerase Activity and TERT Expression During Brain Development in Mice," *J. Neurosci Res.*, 64(3):252-260 (2001).

Kruk et al., "Telomere Reduction and Telomerase Inactivation During Neuronal Cell Differentiation," *Biochem. Biophys. Res. Commun.*, 224(2):487-492 (1996).

Lu et al., "Telomerase Protects Developing Neurons Against DNA Damage-Induced Cell Death," *Brain Res. Dev. Brain Res.*, 131(1-2):167-171 (2001).

Roy et al., "Promoter-Targeted Selection and Isolation of Neural Progenitor Cells From the Adult Human Ventricular Zone," *J. Neurosci. Res.*, 59(3):321-331 (2000).

Wang et al., "Promoter-Based Isolation and Fluorescence-Activated Sorting of Mitotic Neuronal Progenitor Cells from the Adult Mammalian Ependymal/Subependymal Zone," *Dev. Neurosci.*, 22(1-2):167-176 (2000).

Zhu et al., "The Catalytic Subunit of Telomerase Neurons Against Amyloid Beta-Peptide-Induced Apoptosis," *J. Neurochem.*, 75(1):117-124 (2000).

Doevendans et al., "The Utility of Fluorescent *In vivo* Reporter Genes in Molecular Cardiology," *Biochem. and Biophys. Res.* 222:352-358 (1996).

Prasher, "Using GFP to See the Light," *Trends in Genetics* 11(8):320-323 (1995).

(Continued)

*Primary Examiner*—Deborah Crouch
(74) *Attorney, Agent, or Firm*—Nixon Peabody LLP

(57) ABSTRACT

The present invention relates to a method of immortalizing progenitor cells by providing a population of progenitor cells (e.g, neural progenitor cells) and immortalizing the progenitor cells either before or after they are enriched or purified. The present invention is also directed to an enriched or purified population of immortalized progenitor cells (e.g., neural progenitor cells).

45 Claims, 11 Drawing Sheets

OTHER PUBLICATIONS

Gloster et al., "The T alpha 1 alpha-tubulin Promoter Specifies Gene Expression as a Function of Neuronal Growth and Regeneration in Transgenic Mice," *J. Neurosci.* 14(12):7319-30 (1994).

Angelichio et al., "Comparison of Several Promoters and Polyadenylation Signals for Use in Heterologous Gene Expression in Cultured Drosophila Cells," *Nuc. Acids Res.* 19(18):5037-43 (1991).

Schatz et al., "Isolation and Characterization of Conditional-lethal Mutations in the TUB1 alpha-tubulin Gene of the Yeast *Saccharomyces cerevisiae*," *Genetics* 120(3):681-95 (1988).

Schatz et al., "Insertions of up to 17 Amino Acids into a Region of alpha-tubulin Do Not Disrupt Function In Vivo," *Mol. Cell Biol.* 7(10):3799-805 (1987).

Schatz et al., "Genetically Essential and Nonessential alpha-tubulin Genes Specify Functionally Interchangeable Proteins," *Mol. Cell Biol.* 6(11):3722-33 (1986).

Schatz et al., "Two Functional alpha-tubulin Genes of the Yeast *Saccharomyces cerevisiae* Encode Divergent Proteins," *Mol. Cell Biol.* 6(11):3711-21 (1986) (abstract).

Largent et al., "Directed Expression of an Oncogene to the Olfactory Neuronal Lineage in Transgenic Mice," *J. Neuroscience* 13(1):300-312 (1993).

Counter et al., "Telomere Shortening Associated with Chromosome Instability is Arrested in Immortal Cells Which Express Telomerase Activity," *The EMBO Journal* 11:1921-1929 (1992).

Hohaus et al., "Telomerase Activity In Human Hematopoietic Progenitor Cells," *Haematologica* 82:262-268 (1997).

Sharma et al., "Differentiation of Immortal Cells Inhibits Telomerase Activity," *Proc. Natl. Acad. Sci. USA* 92:12343-12346 (1995).

Galiana et al., "Proliferation and Differentiation Properties of Biopotent Glial Progenitor Cell Lines Immortalized With the Adenovirus E1A Gene," *J. Neuro. Research* 36:133-146 (1993).

Raymon et al., "Immortalized Human Dorsal Root Ganglion Cells Differentiate Into Neurons With Nocieptive Properties," *J. of Neuroscience* 19:5420-5428 (1999).

Fu et al., "The Catalytic Subunit of Telomerase is Expressed in Developing Brain Neurons and Serves a Cell Survival-Promoting Function," *Journal of Molecular Neuroscience* 14:3-15 (2000).

* cited by examiner

TELOMERASE IMMORTALIZED NEURAL PROGENITOR CELLS

This application claims the benefit of U.S. Provisional Patent Application Ser. No. 60/311,626, filed Aug. 10, 2001, which is hereby incorporated by reference in its entirety.

The subject matter of this application was made with support from the United States Government under grant numbers NINDS R01 NS39559 and NINDS R01 NS33106. The United States Government may have certain rights.

FIELD OF THE INVENTION

The present invention is directed to telomerase immortalized neural stem and progenitor cells and methods for producing them.

BACKGROUND OF THE INVENTION

The damaged brain is largely incapable of functionally significant structural self-repair. This is due in part to the apparent failure of the mature brain to generate new neurons (Korr, H., *Adv Anat Embryol Cell Biol* 61:1–72 (1980); Sturrock, R., *Adv Cell Neurobiol*, vol. 3, Academic Press, New York, p. 1–33 (1982)). However, the absence of neuronal production in the adult vertebrate forebrain appears to reflect not a lack of appropriate neuronal precursors, but rather their tonic inhibition and/or lack of post-mitotic trophic and migratory support. Converging lines of evidence now support the contention that neuronal precursor cells are distributed widely throughout the ventricular subependyma of the adult vertebrate forebrain, persisting across a wide range of species groups (Goldman, S., et. al., *Proc Natl Acad Sci USA* 80:2390–2394 (1983), Reynolds, B., et. al., *Science* 255:1707–1710 (1992); Richards, L., et al., *Proc Natl Acad Sci USA* 89:8591–8595 (1992); Kirschenbaum, B., et al., *Cerebral Cortex* 4:576–589 (1994); Kirschenbaum, B., and Goldman, S., *Proc Natl Acad Sci USA* 92:210–214 (1995); Goldman, S., *The Neuroscientist* 1:338–350 (1995); Goldman, S., In: *Isolation, Characterization and Utilization of CNS stem cells*. F. Gage, Y. Christen, eds., Foundation IPSEN Symposia. Springer-Verland, Berlin, p. 43–65 (1997); and Gage, F., et al., *Ann Rev Neurosci* 18:159–192 (1995); Gage, F., et al., *Proc Natl Acad Sci USA* 92:11879–11883 (1995)). Most studies have found that the principal source of these precursors is the ventricular zone (Goldman, S., et. al., *Proc Natl Acad Sci USA* 80:2390–2394 (1983); Goldman, S., *J Neurosci* 10:2931–2939 (1990); Goldman, S., et al., *J Neuroscience* 12:2532–2541 (1992); Lois, C., et. al., *Proc Natl Acad Sci USA* 90:2074–2077 (1993); Morshead, C., et al., *Neuron* 13:1071–1082 (1994); Kirschenbaum, B., et al., *Cerebral Cortex* 4:576–589 (1994); Kirschenbaum, B., and Goldman, S., *Proc Natl Acad Sci USA* 92:210–214 (1995); Kirschenbaum, B., and Goldman, S., *Soc Neurosci Abstr* 317.8 (1995)), though competent neural precursors have been obtained from parenchymal sites as well (Richards, L., et al., *Proc Natl Acad Sci USA* 89:8591–8595 (1992); Palmer et al., 1996; Pincus, D., et al., *Ann Neurology* 40:550 (1996)). In general, adult progenitors respond to epidermal growth factor (EGF) and basic fibroblast growth factor (bFGF) with proliferative expansion (Reynolds, B., et. al., *Science* 255:1707–1710 (1992); Kilpatrick, T., et. al., *J Neurosci* 15:3563–3661 (1995)), may be multipotential (Vescovi, A., et al., *Neuron* 11:951–966 (1993); Goldman, S., et al., *Molec Cell Neurosci* 7:29–45 (1996)), and persist throughout life (Goldman, S., et al., *Molec Cell Neurosci* 7:29–45 (1996)). In rodents and humans, their neuronal daughter cells can be supported by brain-derived neurotrophic factor (BDNF) (Kirschenbaum, B., and Goldman, S., *Proc Natl Acad Sci USA* 92:210–214 (1995)), and become fully functional in vitro (Kirschenbaum, B., et al., *Cerebral Cortex* 4:576–589 (1994)), like their avian counterparts (Goldman, S., and Nedergaard, M., *Dev Brain Res* 68:217–223 (1992); Pincus, D., et al., *Ann Neurology* 40:550 (1996)). In general, residual neural precursors are widely distributed geographically, but continue to generate surviving neurons only in selected regions; in most instances, they appear to become vestigial (Morshead, C., et. al., *J Neurosci* 12:249–256 (1992)), at least in part because of the loss of permissive signals for daughter cell migration and survival in the adult parenchymal environment.

A major impediment to both the analysis of the biology of adult neuronal precursors, and to their use in engraftment and transplantation studies, has been their relative scarcity in adult brain tissue, and their consequent low yield when harvested by enzymatic dissociation and purification techniques. As a result, attempts at either manipulating single adult-delived precursors or enriching them for therapeutic replacement have been difficult. The few reported successes at harvesting these cells from dissociates of adult brain, whether using avian (Goldman, S., et al., *J Neuroscience* 12:2532–2541 (1992); Goldman, et. al., *Molec. Cell Neurosci.* 7:29–45 (1996)), murine (Reynolds, B., et. al., *Science* 255:1707–1710 (1992)), or human (Kirschenbaum, B., et al., *Cerebral Cortex* 4:576–589 (1994)) tissue, have all reported <1% cell survival. Thus, several groups have taken the approach of raising lines derived from single isolated precursors, continuously exposed to mitogens in serum-free suspension culture (Reynolds, B., et. al., *Science* 255:1707–1710 (1992); Morshead, C., et al., *Neuron* 13:1071–1082 (1994); Palmer, T., et al., *Mol Cell Neurosci* 6:474–486 (1995)). As a result, however, many of the basic studies of differentiation and growth control in the neural precursor population have been based upon small numbers of founder cells, passaged greatly over prolonged periods of time at high split ratios, under constant mitogenic stimulation. The phenotypic potential, transformation state and karyotype of these cells are all uncertain; after repetitive passage, it is unclear whether such precursor lines remain biologically representative of their parental precursors, or instead become transformants with perturbed growth and lineage control.

Cells of adult organs and tissues arise from dividing progenitor cells, which themselves derive from multipotential stem cells, that both divide and are able to give rise to multiple committed progenitor cell phenotypes. Stem cells express the protein telomerase, which acts to permit continued cell division by maintaining the length of chromosomal telomeres. Telomeric shortening, which occurs when telomerase levels fall, acts as a brake upon cell division and expansion (Harley et al. *Nature* 345:458–460 (1990) and Allsopp et al., *Proc. Natl. Acad. Sci.* 89:10114–10118 (1992)). Committed progenitor cells, derived from stem cells but restricted to give rise only to defined cellular subtypes, down-regulate or lose telomerase expression. Human neural progenitors typically down-regulate telomerase activity to undetectable levels by 16 weeks of gestational age (Wright et al., *Proc. Natl. Acad. Sci.* 89:10114–10118 (1996) and Ulaner et al., *Mol. Human Reprod.* 3:769–773 (1997)), or with early passage in vitro (Ostenfeld et al., *Exp Neurol* 164:215–26 (2000)). In the brain, examples of phenotypically restricted progenitor cells include those for oligodendrocytes, spinal cord motor neurons, midbrain dopaminergic, and basal forebrain cholinergic neurons. These clinically-important progenitor cell types have limited capacity for mitotic expansion, at least in part because of their loss of telomerase expression (Wright et al., *Proc. Natl. Acad. Sci.* 89:10114–10118 (1996)). As a result, it has not hitherto been possible to generate mitotically self-renewing populations of such phenotypically-restricted lineages. Thus, whereas the therapeutic utility of embryonic stem cells has suffered from the plethora of cell types generated by multipotential stem cells, the use of phenotypically restricted progenitor cells has instead been constrained by the limited expansion of which these cells are capable.

The present invention is directed to overcoming this deficiency in the art.

SUMMARY OF THE INVENTION

One embodiment of the present invention relates to a method of immortalizing neural progenitor cells by providing a population of neural progenitor cells and immortalizing the population of neural progenitor cells either before or after they are enriched or purified.

Another aspect of the present invention pertains to a method of immortalizing progenitor cells by providing a population of progenitor cells and immortalizing the progenitor cells either before or after they are enriched or purified.

The present invention is also directed to an enriched or purified population of immortalized progenitor cells.

With the present invention, telomerase-immortalized lines of neural progenitor cells, including cells of both spinal cord and forebrain origin, have been obtained. Immortalization has been achieved with both unsorted ventricular zone and presorted, phenotypically pure progenitor cells using retroviral transduction of target cell populations with the gene encoding human TERT (i.e. hTERT: human telomere-extension reverse transcriptase), the rate-limiting subunit of the telomerase RNA-protein complex.

The advent of preparations of neural progenitor and stem cells has led to a number of studies that have investigated their use in injury and disease, typically following their direct implantation into an injury site. Yet these initial studies have shared a number of features that have limited their likely clinical utility. In particular, they have done so with little or no regard to the region of ventricular zone from which they are derived, and whether that sampled region typically generates the types of neurons and glia that are required for the intended treatment. For instance, spinal cord repair may require spinal cord rather than brain-derived cells, because brain progenitors may be specified to quite different phenotypes, both in terms of homeodomain code-dependent positional cues and transmitter repertoires, than progenitors derived from spinal cord regions. Cultured progenitor cells had little expansion capacity in vitro, as a result, neural transplant attempts have been limited to poorly characterized heterogeneous cultures of native tissue dissociates or, at the opposite extreme, to transformed cell lines able to expand, but as phenotypically unstable, functionally incompetent, or neoplastic cells. The field has lacked a means of immortalizing, in a non-oncogenic fashion, phenotypically-restricted cell types of a given fate, such as spinal cord motor neuronal progenitors. In response to this need, the present invention establishes a means of immortalizing cells with hTERT which yields mitotically active but non-transformed cell lines, whose progeny reliably and reproducibly give rise to cells true to the phenotype of their transduced parental progenitor. Using the approach of the present invention, it is possible to derive immortalized lines of human, functionally-competent progenitor cells, each of which gives rise only to very specific cell types with a predefined functional repetoire and positional origin.

BRIEF DESCRIPTION OF THE DRAWINGS

FIG. 7A shows low and high magnification phase images taken 14 days after the first passage at 1 month of this cell line, while FIGS. 7B–C were taken at 6 months and 12 months, respectively, of this cell line. Each line is passaged once per month, with between 6–7 cell doublings/passage, so that the images of FIGS. 7A, B, and C represent approximately 9, 39, and 75 population doublings (PDs), respectively. Immunocytochemistry of hSC11V-TERT cells showed that the line generated neurons exclusively, as indicated by the expression of (βIII-tubulin (FIG. 7E), and MAP2 (FIG. 6). FIGS. 7F and H are the corresponding Hoechst dye labeled nuclei. To date, the hSC11V-TERT line has undergone >120 population doublings (PDs), compared to pBABE-puromycin infected control cells (FIG. 7D), which reached senescence at 55 PDs, as shown in FIG. 7I.

FIGS. 8A–C show fields of MAP2$^+$ neurons generated in a sixth passage hTERT-transduced ventral spinal culture (36–42 doublings), with two examples of Islet-1$^+$/MAP2$^+$ motor neurons among the more abundant Islet1$^-$/MAP-2$^+$ neurons. FIGS. 8B–D are corresponding phase contrast images. FIGS. 8E–F show phase and fluorescent images of these telomerase-immortalized neuronal progenitor cells, after in vitro exposure to BrdU, and triple-immunostaining thereafter for BrdU, nestin and neuronal MAP-2. After 6 passages (appx. 42 doublings), the culture was exposed to BrdU for 6 hrs, then fixed and stained for BrdU, nestin, and neuronal MAP-2. An abundance of BrdU$^+$/nestin$^+$ cells represents dividing progenitors. A large number of MAP2$^+$ neurons are present, but these uniformly failed to incorporate BrdU. Thus, neurons arising in TERT-immortalized cultures derive from mitotic neuronal progenitor cells, but are themselves postmitotic; they do not arise from aberrant replication of established neurons.

In FIG. 9A, RT-PCR shows the expression of transcription factors CHX10, Isl1, Hb9 and Sim1 by bFGF expanded cells from the hSC11-TERT line. Tissue from a 12-week human fetal spinal cord was used as positive control, which is represented in the first lane (T) of each group. The $2^{nd}$ and $3^{rd}$ lane from each group are RT(−) and RT (+) for the hSC11-TERT cells respectively. FIG. 9B shows that differentiation by addition of BDNF, GDNF, and 10% fetal bovine serum (B/D/S) was associated with an increase in the expression of CHX10 mRNA, and a decrease in the expression of NgN2 mRNA. The first lane in each group is the tissue positive control (T). The $2^{nd}$ and 4th lanes of each group are the RT minus (−) of cells maintained in bFGF (F) or BDNF/GDNF/serum (B/D/S), respectively. The $3^{rd}$ and $5^{th}$ lanes of each group show the PCR products of cells maintained in bFGF (F) or BDNF/GDNF/serum (B/D/S), respectively.

FIGS. 10A–C show that some neurons generated by the hSC11-TERT line matured to express choline acetyl transferase (ChAT), the acetylcholine synthetic enzyme of cholinergic neurons. In the ventral spinal cord, only motor neurons are cholinergic. These cells expressed the neuronal protein (lII-tubulin), and some co-expressed the transcription factor Islet-1, which in the ventral spinal cord is typical of motor neurons. FIGS. 10D–E show an example of a MAP-2 defined neuron expressing ChAT. FIG. 10F shows a large proportion of hSC11V-TERT neurons expressed the NMDA-NR1 glutamate receptor. FIGS. 10G–I show functional maturation of the neurons generated by hSC11-TERT line was indicated by a rapid and reversible increase in the cytosolic calcium levels on exposure to KCl (FIG. 10G, baseline; FIG. 10H, after exposure to 60 mM KCl), as well as by their generation of voltage activated sodium currents (FIG. 10I).

In FIG. 11A, karyotypic analysis of hSC11v-TERT cells (n=20 cells) revealed that all of the analyzed cells had a normal diploid karyotype. In FIGS. 11B–C, flow cytometric analysis of propidium iodide (PI) labeled cells revealed that cells from both early $13^{th}$ (FIG. 11B) and late $30^{th}$ (FIG. 11C) passage had normal DNA complements with no hyperploidization. In FIGS. 11D–F, cells from $30^{th}$ passage responded to the S-phase blocker, hydroxyurea, by an increase in percentage of cells in the S-phase (FIG. 11E). They responded to gamma-irradiation, a G1-phase blocker, by an increase in the G1/S ratio (FIG. 11F). FIG. 11D shows percentage distribution of cells in the G0-G1/S/G2-M phase of cells exposed to any of the blockers. FIG. 11G shows that hTERT overexpression did not affect the ability of cells to respond to cell cycle blockers, and that this ability was maintained after multiple passages. Graph shows the relative percentage of cells in the G0-G1, S and G2-M phase in the absence (−) and in response to hydroxyurea (HU) or gamma-irradiation (G) by cells from $13^{th}$ and $30^{th}$ passage respectively.

DETAILED DESCRIPTION OF THE INVENTION

Figure 1:
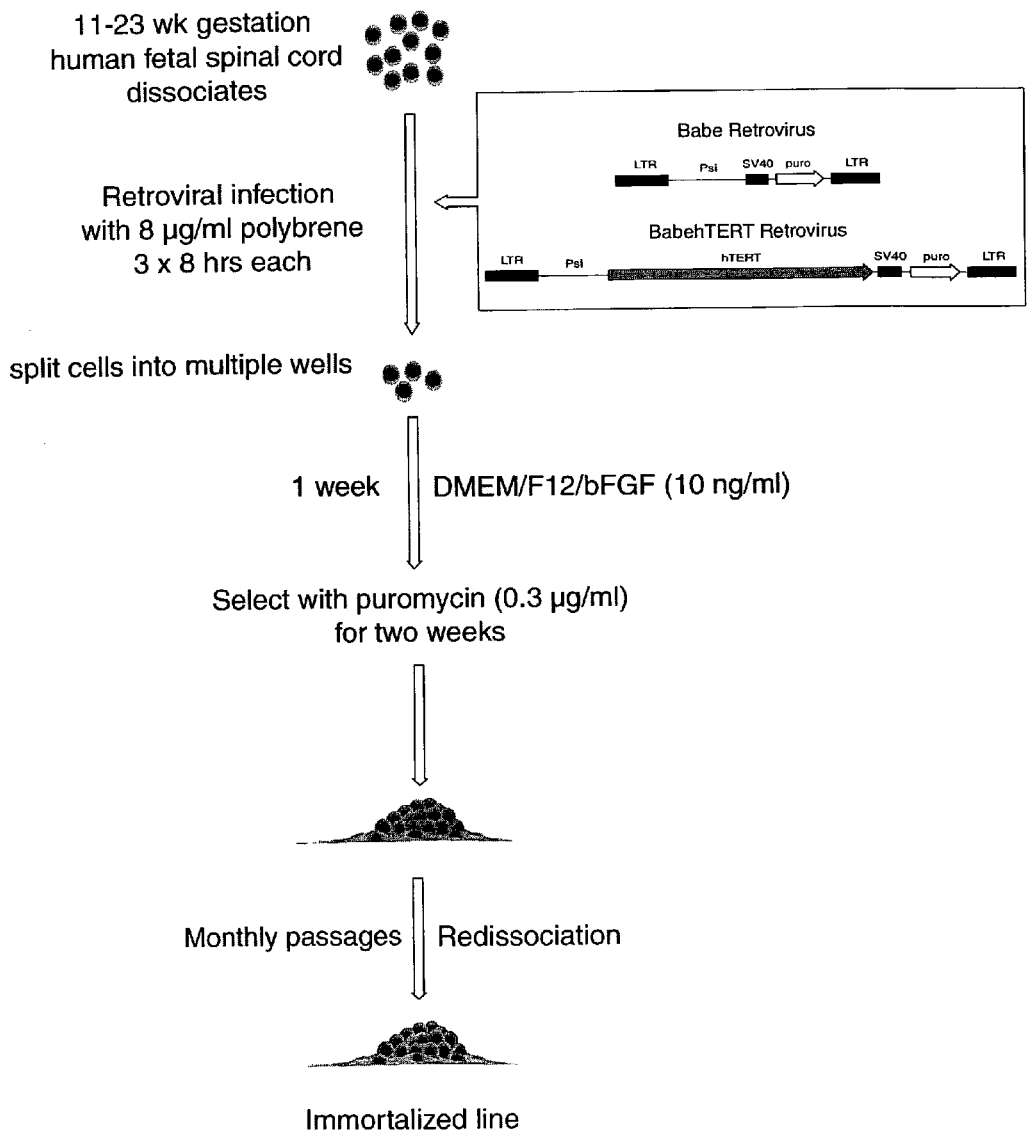
FIG. 1 depicts the production of an immortalized cell line. In this schematic, a dissociated but otherwise unsorted cell population enriched by virtue of specific regional dissection of the neural germinative layer, the ventricular zone, is transduced with retroviral hTERT-puro. Successfully transduced telomerase-overexpressors are then isolated via puromycin.

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized or recombinantly produced nucleic acid molecules).

"Enriched" refers to a cell population that is at least 90% pure with respect to the index phenotype, regardless of its initial incidence in the population from which it was derived. "Purified" refers to a cell population at least 99% pure with respect to the index phenotype, regardless of its initial incidence in the reference population.

One embodiment of the present invention relates to a method of immortalizing neural progenitor cells by providing a population of neural progenitor cells and immortalizing the population of neural progenitor cells either before or after they are enriched or purified.

Another aspect of the present invention pertains to a method of immortalizing progenitor cells by providing a population of progenitor cells and immortalizing the progenitor cells either before or after they are enriched or purified.

The process of selecting progenitors to select a particular cell type from a mixed population of cell types involves using a promoter that functions in the progenitor cells and a nucleic acid encoding a marker protein, as described in U.S. Pat. No. 6,245,564 to Goldman et. al., which is hereby incorporated by reference in its entirety. In particular, this involves providing a mixed population of cell types which population includes progenitor cells of a particular cell type and selecting a promoter which functions in said progenitor cells. A nucleic acid molecule encoding a marker protein under control of said promoter is introduced into the mixed population of cell types, and the population of progenitor cells is allowed to express the marker protein. The cells expressing the marker protein are separated from the mixed population of cells, with the separated cells being the progenitor cells.

The present invention is also directed to an enriched or purified population of immortalized progenitor cells. By use of the process of the present invention, lineage-restricted neural progenitor cells and their progeny can be produced. The neural progenitor cells can be either neuronal progenitor cells, oligodendrocyte progenitor cells, hippocampal progenitor cells, neural stem cells, dopaminergic progenitor cells, chlolinergic progenitor cells, motor neuronal progenitor cells, dorsal neuronal progenitor cells, ventrally-derived neuronal progenitor cells, ventral motor neuronal progenitor cells, ventral mesencephalic neuronal progenitor cells, or mesencephalic dopaminergic progenitor cells. Among the neuronal progenitor cells, those that specifically use dopamine, acetylcholine, serotonin, glutamate, aspartate, norepinephrine, epinephrine, glycine, GABA (gamma amino-butyric acid), cholecystokinin, Substance P, vasoactive intestinal polypeptide, and enkephalin may be immortalized and selectively raised. Such cells can be isolated from the spinal cord, brain, pancreatic islet, or retina. These cells can be from humans and may be of fetal, neonatal, child, or adult origin. Progenitor cells specific for position and region may also be immortalized as such. These include both neuronal and glial progenitor cells positionally-specified to either dorsal or ventral portions of one or more of the following regions: the forebrain, hypothalamus, midbrain, pons, medulla, and spinal cord.

Any neural progenitor cell which one desires to separate from a plurality of cells and immortalize can be selected in accordance with the present invention, as long as a promoter specific for the chosen cell is available. "Specific", as used herein to describe a promoter, means that the promoter functions only in the chosen cell type. A chosen cell type can refer to different types of cells or different stages in the developmental cycle of a progenitor cell. For example, the chosen cell may be committed to a particular adult neural cell phenotype and the chosen promoter only functions in that neural progenitor cell; i.e. the promoter does not function in adult neural cells. Although committed and uncommitted neural progenitor cells may both be considered neural progenitor cells, these cells are at different stages of neural progenitor cell development and can be separated and immortalized according to the present invention if the chosen promoter is specific to the particular stage of the neural progenitor cell. Those of ordinary skill in the art can readily determine a cell of interest to select based on the availability of a promoter specific for that cell of interest.

Illustrative of possible cell and promoter combinations which can be used in the subject invention are the following: a developing or regenerating neuron and a MAP-1B promoter (Liu and Fischer, *Gene* 171:307–308 (1996), which is hereby incorporated in its entirety); a neuronal progenitor cell and an NCAM promoter (Holst et al., *J Biol Chem* 269:22245–22252 (1994), which is hereby incorporated in its entirety); a neuronal progenitor cell and an HES-5 HLH protein promoter (Takebayashi et al., *J Biol Chem* 270:1342–1349 (1995), which is hereby incorporated in its entirety); a neuronal progenitor cell and an α1-tubulin promoter (Gloster, A., et al., *J Neurosci* 14:7319–7330 (1994), which is hereby incorporated in its entirety); a developing or regenerating neuron and an α1-tubulin promoter (Gloster, A., et al., *J Neurosci* 14:7319–7330 (1994), which is hereby incorporated in its entirety); a developing or regenerating neuron and an α-internexin promoter (Ching et al., *J Biol Chem* 266:19459–19468 (1991), which is hereby incorporated in its entirety); a developing or regenerating neuron and a GAP-43 promoter (Starr et al., *Brain Res* 638:211–220 (1994), which is hereby incorporated in its entirety); an oligodendrocyte progenitor cell and a JC virus minimal core promoter (Krebs et al., *J Virol* 69:2434–2442 (1995), which is hereby incorporated in its entirety); an oligodendrocyte progenitor cell and a cyclic nucleotide phosphorylase II promoter (Scherer et al., *Neuron* 12:1363–1375 (1994)); neural progenitor cells and a nestin enhancer (Keyoung et al., *Nature Biotechnol.* 19:843–50 (2001)), and neural progenitor cells and a musashi promoter (Keyoung et al., *Nature Biotechnol.* 19:843–50 (2001)).

More specific neuronal phenotypes, typical of given neurotransmitters may be similarly derived using promoters for genes that are transcribed only in progenitors specific for neurons producing that neurotransmitter. The promoters for tyrosine hydroxylase (for dopaminergic neurons: Matsushita et al., *J. Neurochem.* 82:295–304 (2002), which is hereby incorporated by reference), choline acetyltransferase (for cholinergic neurons: Bausero et al. *Neuro Report* 4:287–290 (1993), which is hereby incorporated by reference), glutamic acid decarboxylase (for GABAergic neurons: Pedersen et al., *DNA Seq.* 11:485–99 (2001), which is hereby incorporated by reference), may thereby be used to identify and enrich dopaminergic, cholinergic and GABAergic neuronal progenitor cells, respectively. Similarly, progenitors specific for given brain and spinal cord regions and hence specified for specific cell populations of the central nervous system (CNS), may be selected using promoters for genes transcriptionally active only in that region of the CNS. By way of example, the promoters for those genes encoding the MNR2 or Hb9 genes may allow identification—and hence promoter-specified, GFP-based FACS extraction—of cells committed to motor neuron phenotype (Tanabe et al. *Cell* 95:67–80 (1998); Wichterle et al., *Cell*, published online Jul. 17, 2002, which are hereby incorporated by reference). The promoter for the sox2 homeodomain gene permits identification of a variety of dorsal neuronal populations, which may be more tightly defined by using specific enhancers within the regulatory regions of the gene (Zappone et al., *Development* 127:2367–2382 (2000), which is hereby incorporated by reference). Promoters for regionally-specifying bHLH proteins may be similarly employed. The neurogenin2 promoter may be used to select ventrally-derived neuronal phenotypes, and specific enhancers within the neurogenin gene permit selection to be targeted to even more tightly-defined cell populations, such as the ventral motor neuron and ventral mesencephalic pools (Simmons et al., *Developmental Biology* 229: 327–339 (2001), which is hereby incorporated by reference). In addition, progenitors specific for given lineages may be selected on the basis of promoters for genes transcribed selectively in founders of that lineage. The promoters for both Nkx2.2 and olig2 may recognize oligodendrocyte progenitor cells (Fu et al. *Development* 129:681–693 (2002) and Zhou et al. *Neuron* 31: 791–807 (2001), which are hereby incorporated by reference), since these transcription factors are expressed in the oligodendroglial lineage at earlier stages than the CNP2 enhancer discussed previously. Combinations of these strategies may be employed, using promoters for genes that are expressed only during discrete time windows in given regions, which then give rise only to certain neurotransmitter phenotypes. One example is the use of a specific enhancer within the neurogenin gene that permits selection to be targeted to mesencephalic dopaminergic progenitors (Simmons et al., *Developmental Biology* 229: 327–339 (2001), which is hereby incorporated by reference).

Having determined the cell of interest and selected a promoter specific for the cell of interest, a nucleic acid molecule encoding a protein marker, preferably a green fluorescent protein under the control of the promoter is introduced into a plurality of cells to be sorted.

The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (U.S. Pat. No. 5,491,084 to Chalfie et al., which are hereby incorporated in their entirety). A plasmid designated pGFP10.1 has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 75547 on Sep. 1, 1993. This plasmid is commercially available from the ATCC and comprises a cDNA which encodes a green fluorescent protein (GFP) of *Aequorea victoria* as disclosed in U.S. Pat. No. 5,491,084 to Chalfie et al., which is hereby incorporated in its entirety. A mutated form of this GFP (a red-shifted mutant form) designated pRSGFP-C1 is commercially available from Clontech Laboratories, Inc. (Palo Alto, Calif.).

The plasmid designated pTα1-RSGFP has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 98298 on Jan. 21, 1997. This plasmid uses the red shifted GFP (RS-GFP) of Clontech Laboratories, Inc. (Palo Alto, Calif.), and the Tα1 promoter sequence provided by Dr. F. Miller (Montreal Neurological Institute, McGill University, Montreal, Canada). In accordance with the subject invention, the Tα1 promoter can be replaced with another specific promoter, and the RS-GFP gene can be replaced with another form of GFP, by using standard restriction enzymes and ligation procedures.

Mutated forms of GFP that emit more strongly than the native protein, as well as forms of GFP amenable to stable translation in higher vertebrates, are now available and can be used for the same purpose. The plasmid designated pTα1-GFPh has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 98299 on Jan. 21, 1997. This plasmid uses the humanized GFP (GFPh) of Zolotukhin and Muzyczka (Levy, J., et al., *Nature Biotechnol* 14:610–614 (1996), which is hereby incorporated in its entirety), and the Tα1 promoter sequence provided by Dr. F. Miller (Montreal). In accordance with the subject invention, the Tα1 promoter can be replaced with another specific promoter, and the GFPh gene can be replaced with another form of GFP, by using standard restriction enzymes and ligation procedures. Any nucleic acid molecule encoding a fluorescent form of GFP can be used in accordance with the subject invention.

Standard techniques are then used to place the nucleic acid molecule encoding GFP under the control of the chosen cell specific promoter. Generally, this involves the use of restriction enzymes and ligation.

The resulting construct, which comprises the nucleic acid molecule encoding the GFP under the control of the selected promoter (itself a nucleic acid molecule) (with other suitable regulatory elements if desired), is then introduced into a plurality of cells which are to be sorted. Techniques for introducing the nucleic acid molecules of the construct into the plurality of cells may involve the use of expression vectors which comprise the nucleic acid molecules. These expression vectors (such as plasmids and viruses) can then be used to introduce the nucleic acid molecules into the plurality of cells.

Various methods are known in the art for introducing nucleic acid molecules into host cells. These include: 1) microinjection, in which DNA is injected directly into the nucleus of cells through fine glass needles; 2) dextran incubation, in which DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell; 3) calcium phosphate coprecipitation, in which cells efficiently take in DNA in the form of a precipitate with calcium phosphate; 4) electroporation, in which cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA); 5) liposomal mediated transformation, in which DNA is incorporated into artificial lipid vesicles, liposomes, which fuse with the cell membrane, delivering their contents directly into the cytoplasm; 6) biolistic transformation, in which DNA is absorbed to the surface of gold particles and fired into cells under high pressure using a ballistic device; and 7) viral-mediated transformation, in which nucleic acid molecules are introduced into cells using viral vectors. Since viral growth depends on the ability to get the viral genome into cells, viruses have devised efficient methods for doing so. These viruses include retroviruses, lentivirus, adenovirus, herpesvirus, and adeno-associated virus.

As indicated, some of these methods of transforming a cell require the use of an intermediate plasmid vector. U.S. Pat. No. 4,237,224 to Cohen and Boyer, which is hereby incorporated in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al., *Molecular Cloning: A Laboratory Manual,* 2d Edition, Cold Spring Harbor Laboratory Press, Cold Spring Harbor, N.Y. (1989), which is hereby incorporated in its entirety.

In accordance with one of the above-described methods, the nucleic acid molecule encoding the GFP is thus introduced into a plurality of cells. The promoter which controls expression of the GFP, however, only functions in the cell of interest. Therefore, the GFP is only expressed in the cell of interest. Since GFP is a fluorescent protein, the cells of interest can therefore be identified from among the plurality of cells by the fluorescence of the GFP.

Any suitable means of detecting the fluorescent cells can be used. The cells may be identified using epifluorescence optics, and can be physically picked up and brought together by Laser Tweezers (Cell Robotics Inc., Albuquerque, N. Mex.). They can be separated in bulk through fluorescence activated cell sorting, a method that effectively separates the fluorescent cells from the non-fluorescent cells.

The method of the subject invention thus provides for the isolation and enrichment of neural precursors from embryonic and adult brain. Specifically, fluorescence-activated cell sorting of subependymal cells transfected with green fluorescent protein driven by the neuronal Tα1 tubulin promoter is provided. Tα1, a member of the α-tubulin multigene family, is localized almost exclusively to the nervous system, within which it appears specific for neurons (Miller, F., et al., *J Cell Biol* 105:3065–3073 (1987), Miller, F., et al., *J Neurosci* 9:1452–1463 (1989); Gloster, A., et al., *J Neurosci* 14:7319–7330 (1994), which are hereby incorporated in their entirety). Though most abundant in young neurons extending neurites, it is first expressed earlier in neuronal ontogeny, including in VZ cells (Miller, F., et al., *J Cell Biol* 105:3065–3073 (1987), which is hereby incorporated in its entirety). The 1.1 kb 5' flanking region from the Tα1 gene contains those sequence elements responsible for specifying Tα1 expression to embryonic neurons, and for regulating its expression as a function of growth (Gloster, A., et al., *J Neurosci* 14:7319–7330 (1994), which is hereby incorporated in its entirety). Transgenic mice with the 1.1 kb 5' flanking region fused to a nuclear lacZ reporter manifested expression of the Tα1 promoter-driven transgene only within the developing central nervous system, and then only in neurons and the neural VZ, suggesting that Tα1 tubulin promoter was expressed by premitotic VZ precursor cells, as well as their young neuronal progeny (Gloster, A., et al., *J Neurosci* 14:7319–7330 (1994), which is hereby incorporated in its entirety).

As an alternative or an addition to sorting cells based on the transduction and expression of a marker protein under control of a cell-specific promoter, sorting can be carried out by separating cells based on proteinaceous surface markers naturally present on progenitor cells of a specific type. For example, the surface marker A2B5 is an initially expressed early oligodendrocyte marker. See Nunes et al., "Identification and Isolation of Multipotential Neural Progenitor Cells from the Adult Human White Matter, "*Soc. Neurosci. Abstr.* (2001), which is hereby incorporated by reference. A further example is the AC133 surface marker for neural progenitor cells. See Uchida et al., "Direct Isolation of Human Central Nervous System Stem Cells," *Proc. Natl. Acad. Sci.* 97:14720–25 (2000), which is hereby incorporated by reference. Using an antibody specific to those markers, progenitor cells of those phenotypes can be separated from a mixed population of cell types. Such antibodies can be labeled with a fluorescent tag to facilitate separation of cells to which they bind. Alternatively, the antibodies can be attached to paramagnetic beads so that cells which bind to the bead through the attached antibodies can be recovered by a biomagnetic separation process. Separation based on the presence of a natural marker can be use alone as an alternative to sorting cells based on the transduction and expression of a marker protein under control of a cell-specific promoter to produce a high yield of recovered cells. Alternatively, separation based on the presence of a natural marker can be used either before or after sorting cells based on the transduction and expression of a marker protein under control of a cell-specific promoter to produce a high cell population with a high purity of the desired cells.

A hybridoma producing monoclonal antibodies specific to Gq ganglioside, designated A2B5 has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. CRL-01520.

A hybridoma producing monoclonal antibodies specific to a surface determinant, designated AC133, has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. HB-12346.

To establish a means of immortalizing phenotypically-restricted progenitor cells, such progenitor cells must also be transduced with a nucleic acid molecule encoding a human telomerase reverse transcriptase (hTERT). Such nucleic acid molecules are described in U.S. Pat. No. 6,166,178 to Cech et al., which is hereby incorporated by reference in their entirety. Transduction with a nucleic acid molecule encoding a human telomerase reverse transcriptase is achieved in substantially the same manner as is used to transduce such cells with a GFP-encoding nucleic acid, except that any promoter (not necessarily a cell-specific promoter) which will achieve expression can be used. As a result, telomerase-immortalized lines of phenotypically-committed human neural progenitor cell types can be established. For example, a VSVg-pseudotyped retrovirus encoding human telomerase reverse transcriptase (hTERT, in pBABE-puro under CMV control) can be used to transduce neural progenitor cells to constitutively express telomerase. As cellular targets for hTERT overexpression, fresh ventricular zone dissociates, derived from both forebrain and spinal cord ventricular zone sampled from second trimester human fetuses, can be used. For this purpose, selectively dissected regions and developmental timepoints at which one phenotype or another predominate can be utilized.

FIGS. 1–5 depict various strategies for carrying out the process of the present invention.

Figure 2:
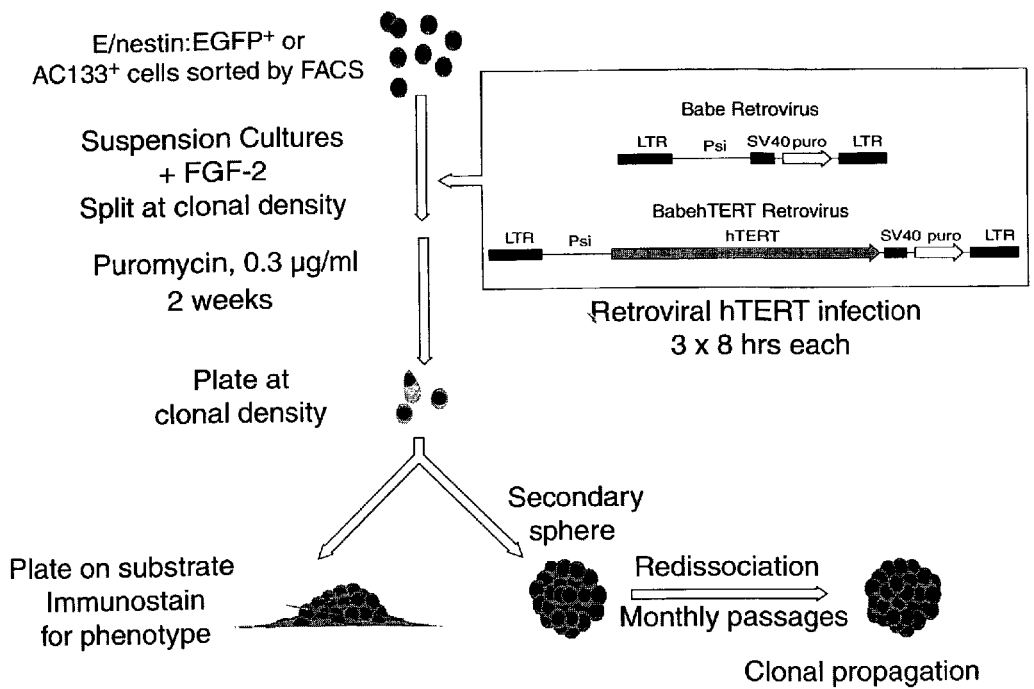
FIG. 2 shows a second embodiment for the production of an enriched population of immortalized neural progenitor cells, using promoter-specified, GFP-based FACS selection of target progenitor cells, prior to hTERT transduction of the sorted progenitor cell pool. In this illustration, a FACS-sorted cell population is transduced with retroviral hTERT-puro. Successfully transduced telomerase-overexpressors are then isolated via puromycin selection.
Figure 3:
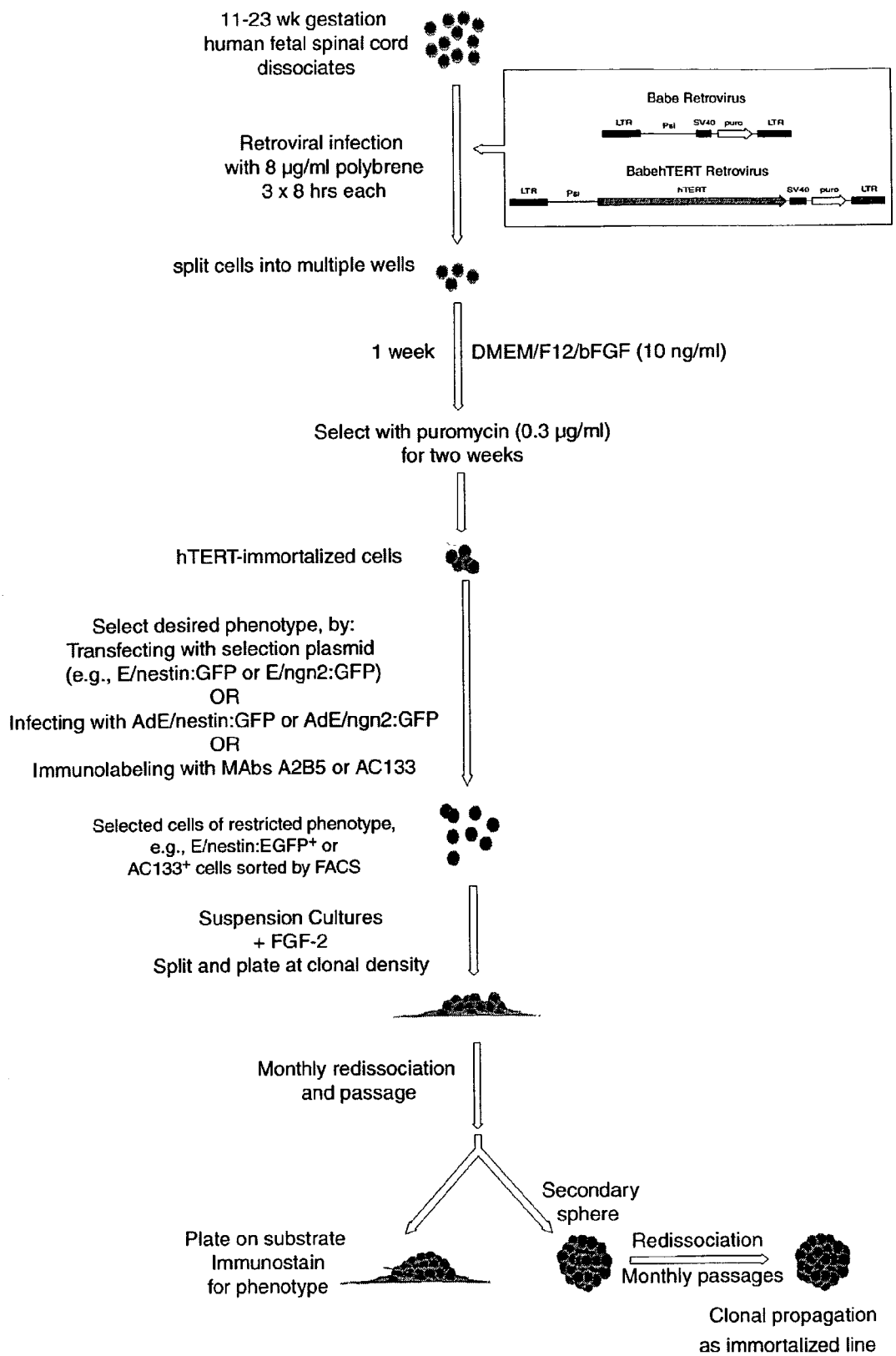
FIG. 3 shows another embodiment for the production of an enriched population of immortalized, neural progenitor cells. In this schematic, a dissociated but otherwise unsorted cell population, enriched by virtue of specific regional dissection of the ventricular zone, is transduced with retroviral hTERT-puro. Successfully transduced telomerase-overexpressors are then isolated via puromycin selection. After selection, the immortalized cells are transfected with vectors encoding GFP placed under the control of cell type-specific promoters. Upon GFP expression by the cognate lines or clones within the larger population, GFP-based FACS is then used to select the target cell type of interest.

FIGS. 1–3 depict several strategies for immortalizing neural progenitor cells. These differ in when and how the cell-type selection is performed with respect to when the cells are transduced with hTERT.

FIG. 1 depicts the production of an immortalized cell line. In this schematic, a dissociated but otherwise unsorted cell population enriched by virtue of specific regional dissection of the neural germinative layer, the ventricular zone, is transduced with retroviral hTERT-puro. This procedure starts with transducing dissociates of 9–23 week gestation human fetal spinal cord, by infection with a retrovirus containing the cassette designated pBabe-hTERT-puro. The infected cells are split into multiple wells and successfully transduced telomerase-overexpressors are then isolated via puromycin selection. Successfully-transduced cells exhibit preferential survival in puromycin. After further incubation expansion and repetitive passaging, telomerase-immortalized clones exhibit and can be selected by their preferential expansion. The recovered phenotype may then be identified by antigenic characterization and transcriptional analysis.

This most basic among the embodied strategies does not include cell-type specific phenotypic selection. FIGS. 2–5 represent elaborations of this approach, in that all include a selection step, either before or after the hTERT transduction step.

FIG. 2 shows a second embodiment for the production of an enriched population of immortalized neural progenitor cells, using promoter-specified, GFP-based FACS selection of target progenitor cells, prior to hTERT transduction of the sorted progenitor cell pool. In this illustration, a FACS-sorted cell population is transduced with retroviral hTERT-puro. In this example, cells of one phenotype are first extracted as such by sorting by FACS, using either promoter-specified GFP expression, or surface markers typical, of specific phenotypes, such as A2B5 or AC133, as described above. The resulting cells are cultured, infected with the Babe-hTERT-containing retrovirus, split at clonal density, and plated to produce primary spheres. Successfully transduced telomerase-overexpressors are then isolated via puromycin selection. These are subsequently allowed to re-expand. The resulting cells can then be plated and immunostained for phenotype, or allowed to form secondary spheres, which may be redissociated and further passaged.

FIG. 3 shows another embodiment for the production of an enriched population of immortalized, neural progenitor cells. In this schematic, a dissociated but otherwise unsorted cell population, enriched by virtue of specific regional dissection of the ventricular zone, is transduced with retroviral hTERT-puro. Successfully transduced telomerase-overexpressors are then isolated via puromycin selection. After selection, the immortalized cells are transfected with vectors encoding GFP placed under the control of cell type-specific promoters. Upon GFP expression by the cognate lines or clones within the larger population, GFP-based FACS is then used to select the target cell type of interest.

Figure 4:
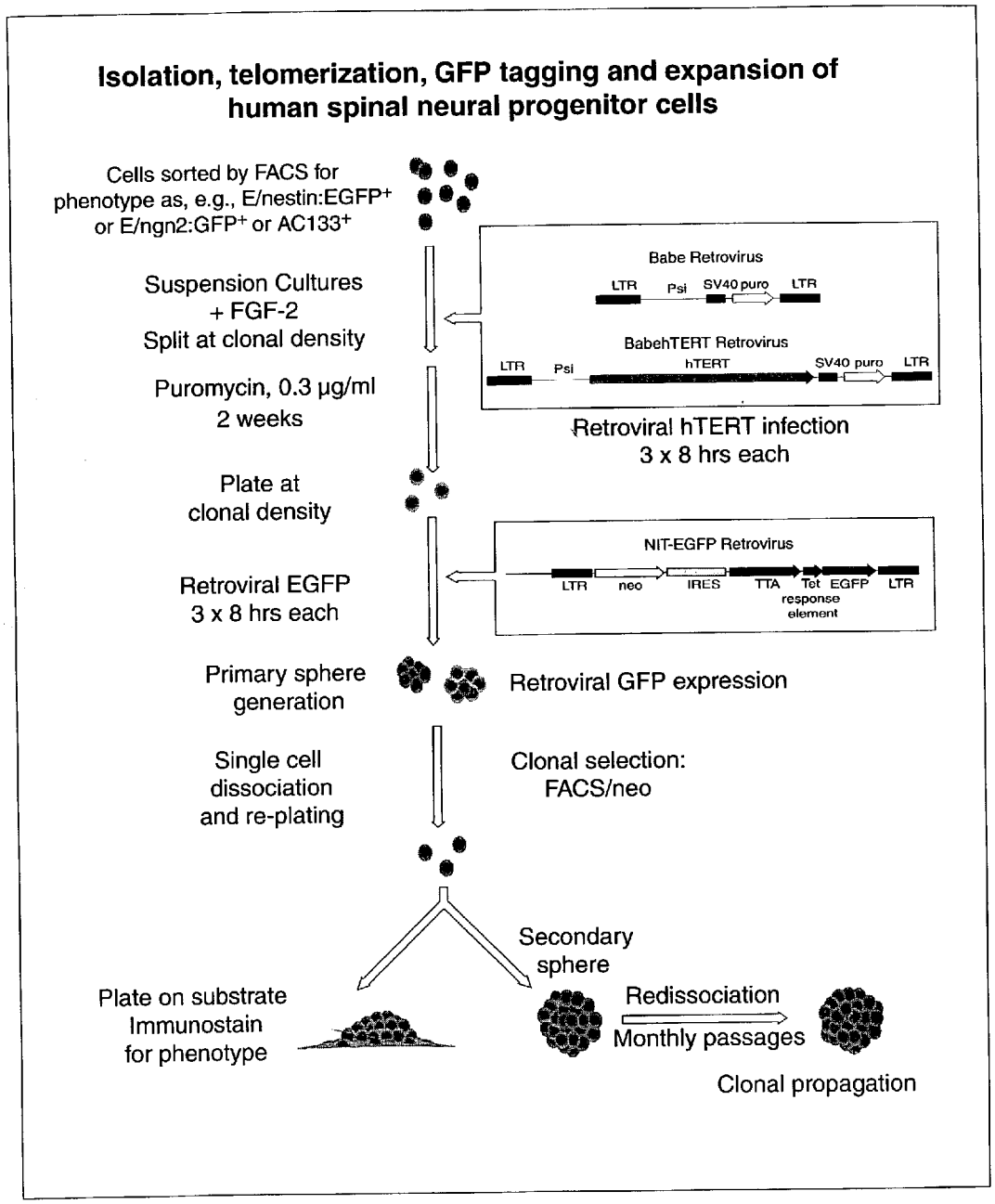
FIG. 4 shows an embodiment for the production of genetically-tagged immortalized neural progenitor cells, suitable for secondary selection and clonal analysis. In this illustration, a FACS-sorted cell population is transduced with retroviral hTERT-puro. Successfully transduced telomerase-overexpressors are then isolated via puromycin selection. After the GFP fluorescence of the transient transfections for phenotypic identification and FACS has sufficiently abated, the telomerase-immortalized lines within the population are then infected again, this time with retroviral-delivered GFP for the purpose of lineage tagging.
Figure 5:
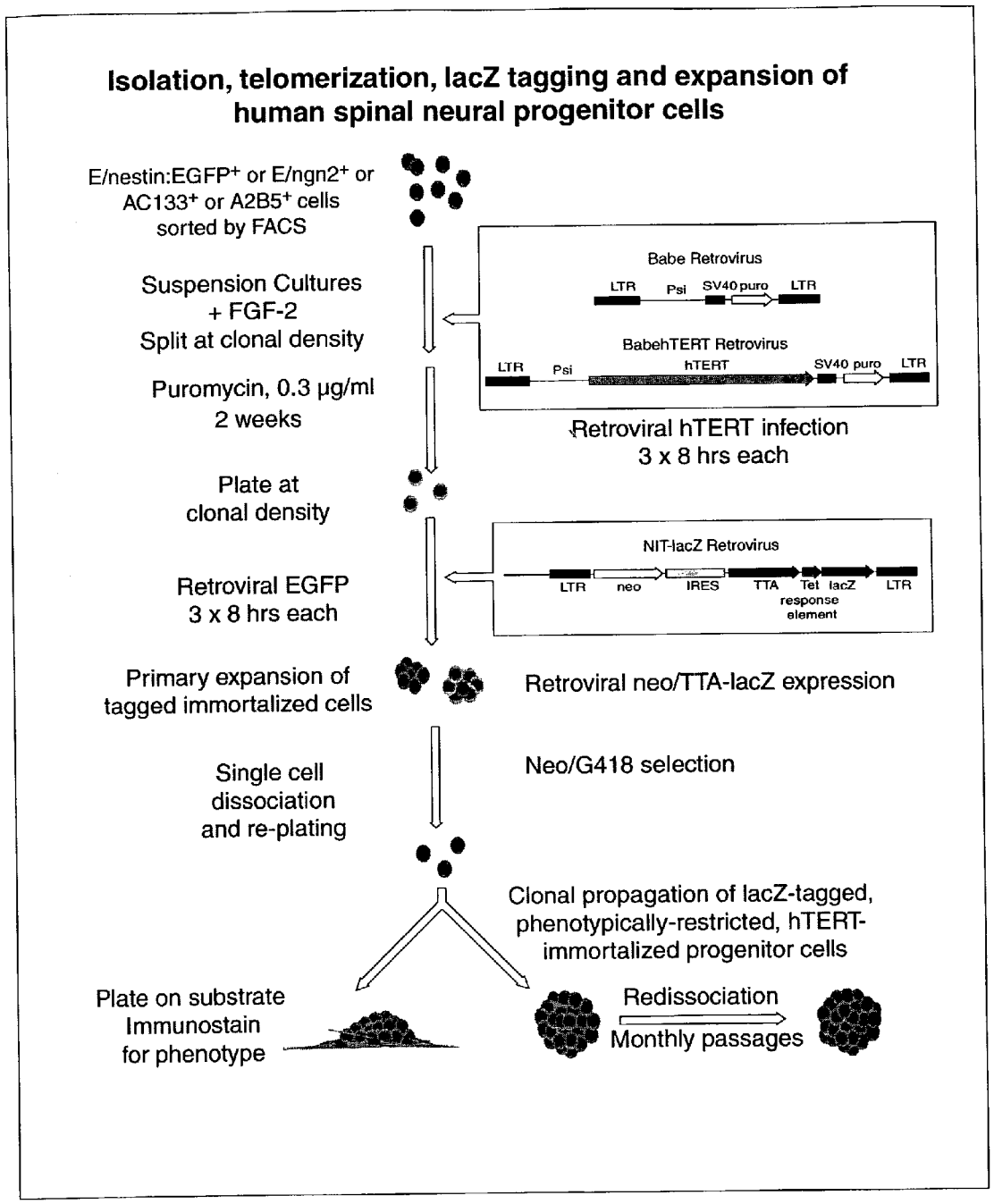
FIG. 5 shows an embodiment for the production of genetically-tagged immortalized neural progenitor cells, suitable for clonal analysis and transplantation. In this illustration, a FACS-sorted cell population is transduced with retroviral hTERT-puro. Successfully transduced telomerase-overexpressors are then isolated via puromycin selection. After the GFP fluorescence of the transient transfections for phenotypic identification and FACS has sufficiently abated, the telomerase-immortalized lines within the population are then infected again, this time with retroviral-delivered lacZ for the purpose of genetic tagging antecedent to clonal analysis or transplantation.

FIGS. 4 and 5 show embodiments for the genetic tagging of hTERT-immortalized progenitors, for the purposes of following derivative lineages and assessing the fate of transplanted cells.

FIG. 4 shows an embodiment for the production of genetically-tagged immortalized neural progenitor cells, suitable for secondary selection and clonal analysis. In this illustration, a FACS-sorted cell population is transduced with retroviral hTERT-puro. Successfully transduced telomerase-overexpressors are then isolated via puromycin selection. After the GFP fluorescence of the transient transfections for phenotypic identification and FACS has sufficiently abated, the telomerase-immortalized lines within the population are then infected again, this time with retroviral-delivered GFP for the purpose of lineage tagging.

FIG. 5 shows an embodiment for the production of genetically-tagged immortalized neural progenitor cells, suitable for clonal analysis and transplantation. In this illustration, a FACS-sorted cell population is transduced with retroviral hTERT-puro. Successfully transduced telomerase-overexpressors are then isolated via puromycin selection. After the GFP fluorescence of the transient transfections for phenotypic identification and FACS has sufficiently abated, the telomerase-immortalized lines within the population are then infected again, this time with retroviral-delivered lacZ for the purpose of genetic tagging antecedent to clonal analysis or transplantation.

EXAMPLES

Example 1

Spinal Cord Preparation and Culture

Normal human fetal spinal cords were obtained in the course of elective abortions. Cervical, thoracic and lumbar regions of the spinal cord were dissected out in $Ca^{2+}/Mg^{2+}$-free HBSS. For later fetuses (11 and 13 week g.a.), the spinal cord was divided longitudinally into ventral and rostral strips before rostrocaudal segmentation. Whereas the spinal neuroepithelium was used as the source of progenitors in the 13 and 18 week g.a. samples, the entire thickness of the cord was used in the 9 and 11 week samples, which proved too small for selective removal of the neuroepithelium. The dissected tissue was minced, suspended in PIPES buffer (in mM: 120 NaCl, 5 KCl, 25 glucose, and 20 PIPES), then digested in papain—PIPES (11.4 U/ml papain; Worthington, Freehold, N.J.) and DNase I (10 U/ml; Sigma, St. Louis, Mo.) for 40 min while shaking at 37° C. The cells were collected by centrifugation at 200×g in an IEC Centra-4B centrifuge, resuspended in DMEM/F-12/N1 with DNase I (10 U/ml), and incubated for 30 min at 37° C. The samples were again spun, and their pellets recovered in 2 ml of DMEM/F-12/N1. These were dissociated by sequentially triturating 20, 10, and 5 time through glass Pasteur pipettes fire-polished to decreasing bore diameters. The cells were passed through a 40 µm mesh into DMEM/F-12/N1, with 10% platelet-depleted fetal bovine serum (PD-FBS; Cocalico Biologicals, Reamstown, Pa.) to stop the enzymatic dissociation. The cells were then suspended in DMEM/F12/N1 supplemented with bFGF (10 ng/ml, Sigma) and plated in 6 well tissue culture dishes at $1\times10^5$ cells/ml.

Example 2

Retroviral hTERT Propagation and Infection

For immortalization, cells were infected with VSVg-pseudotyped retrovirus encoding hTERT in pBABE-puro under CMV control. Equal number of cells from each tissue sample were also infected with control retrovirus with the vector pBABE-puro without hTERT. This served as an internal control to differentiate against any native non-immortalized progenitors. The cells were treated with the viral supernatants thrice at 8-hourly intervals with polybrene (8 µg/ml). Following viral infection, the cells will be resuspended in fresh medium and redistributed at lower densities to decrease to possibility of multiple transfectants in same culture dish.

Example 3

Selection

One-two weeks after the viral infection, positively transduced cells were selected in 0.4 µg/ml puromycin (Sigma) for 2 weeks. Successful selectants from both retroviral pBabe:puro and pBabe:hTERT-puro infected cells were isolated and propagated in DMEM/F12/N1 supplemented with bFGF (10 ng/ml, Sigma).

Example 4

TRAP Assay

The cultured cells were solubilized in 100 µl of CHAPS lysis buffer (10 mM Tris-HCl pH 7.5, 1 mM MgCl$_2$, 1 mM EGTA, 0.1 mM Benzamidine, 5 mM β-mercaptoethanol, 0.5% CRAPS, 10% Glycerol). Five hundred nanograms of protein from each sample were used in the TPAP assay. The assay mixture contained the following, in TRAP buffer (20 mM Tris-HCl, 1.5 mM MgCl$_2$, 63 mM KCl, 0.005% Tween-20, 1 mM EGTA, 0.1 µg/ml BSA, pH 8.3): 50 µM dNTP, 2 µg/ml of $^{32}$P-end-labeled TS primer (5'-AATCCGTCGAG-CAGAGTT-3' (SEQ. ID. NO: 1), 2 µg/ml of reverse primer (Intergen, Gaithersburg, Md.), 1 µg of T4 gene-32 protein (Boehringer Mannheim, Indianapolis, Id.), and 5 U/µl Taq polymerase (Promega). To test the specificity of the telomerase assay, 2 µl of cell extracts pre-incubated at 85° C. for 10 min were added to heat-inactivated control mixtures. As positive controls for telomerase activity, 2 µl of 250 cells/µl 293 cells were used. All samples were first incubated at 30° C. for 30 min to allow telomerase-mediated extension of the TS primer. The samples were then amplified by PCR (94° C. for 30 sec denaturation, 55° C. for 30 sec annealing, and 72° C. for 1 min extension, for 30 cycles). The products were resolved on a 12.5% non-denaturing PAGE gel, followed by autoradiography.

Example 5

Transcription Factor PCR

RNA from cells and 12 week spinal cord (control) was extracted using the RNeasy Mini Kit (Qiagen). RT reaction was performed with Oligo-dT primer (Invitrogen) using Thermoscript kit (Invitrogen) with equal amounts of RNA for each group. The primers used for the PCR were:

```
Ngn2:
5'-TTCGCCCACAACTACATCTG-3', and    (SEQ. ID. NO:2)
5'-GGAAAGGGAACCCACTAAGG-3';        (SEQ. ID. NO:3)

Hb9:
5'-CGAGGACGACGAGGACCATTT-3' and    (SEQ. ID. NO:4)
5'-CGGTTCTTCTCACACGCACTC-3';       (SEQ. ID. NO:5)

Islet-1:
5'-GCAGCATCGGCTTCAGCAAG-3' and     (SEQ. ID. NO:6)
5'-GTAGCAGGTCCGCAAGGTG-3';         (SEQ. ID. NO:7)

Chx10:
5'-CAGCTGGAGGACATGGCTTA-3' and     (SEQ. ID. NO:8)
5'-CAGCATGGTCCAGAGTCAGA-3';        (SEQ. ID. NO:9)

Sim1:
5'-GTGAAGTGCCACATGACAGC-3' and     (SEQ. ID. NO:10)
5'-GCTGCCTTACAAACCAGGAA-3';        (SEQ. ID. NO:11)

βactin,
5'-CCACACCTTCTACAATGAGCTG-3' and   (SEQ. ID. NO:12)
5'-AGCCTGGATAGCAACGTACATG-3'.      (SEQ. ID. NO:13)
```

The PCR reactions were conducted using an LA Taq (Takara Bio). The PCR conditions were: 95° C. 3 min, 95° C./1 min, 60° C./1 min, and 72° C./1 min for 36–39 cycles, followed by 72° C. for 15 min.

Example 6

Insertion Site Analysis

To determine whether the several phenotypes of neurons generated by these hTERT-immortalized progenitors were clonally-derived, Southern blotting of the hTERT insertion site was used to characterize the homogeneity—or lack thereof—of the insert sequence among cells within single spheres. Clonal analysis suggested the co-derivation of several spatially non-overlapping neuronal phenotypes from single progenitor cells of the human spinal neuroepithelium.

Example 7

Transfection

Cells were transfected with plasmid P/ngn2:EGFP or control plasmid P/CMV:GFP (for determination of transfection efficiency) using Effectene (Quiagen) for 6 hrs. The transfection was terminated by changing to DMEM/F12/N1 with 10% PD-FBS. After 2 hrs, the cells were returned to DMEM/F12/N1 supplemented with bFGF.

Example 8

Flow Cytometry

Flow cytometry analysis of positive cells was performed on a FACS Vantage (Becton-Dickinson), using its Cell Quest analysis package. Cells ($5 \times 10^6$/ml) were analyzed by forward and right-angle (side) scatter, and for fluorescence through a 530±15 nm bandpass filter, as they traversed the beam of an argon ion laser (488 nm, 100 mW). Untransfected cells were used to calibrate the background; a false positive rate of 1% was accepted as cutoff.

Example 9

Population Doubling

Once the lines were established, the population doubling was determined by using a 3T3 protocol. The lines were split every 4–5 days at a density of 50,000 cells/ml (1 million cells per well of a 6 well plate).

Example 10

Cell Cycle Analysis

Cultures were labeled with BrdU (10 ug/ml) for 6 hours. To check for the cells' response to S-phase blockers, the cells were treated with gamma-irradiation (40 Gy) or exposed to hydroxy-urea (5 mM) for 3 days followed by a BrdU pulse of 6. Following trypsinization to obtain single cell suspension, the cells were fixed in cold 70% ethanol, treated with 2N HCl for 20 mins, neutralized 2M sodium-borate and labeled with rat anti-BrdU antibody, followed by FITC-conjugated goat anti-rat secondary antibody. After counter-staining with propidium iodide (40 ug/ml), the cells were analyzed for DNA content on a Coulter-Elite flow cytometer, and the percentage of cells in G1, S and G2/M phase was determined by the Watson (Pragmatic) model using the FlowJo program.

Example 11

Karyotyping

To establish whether the lines are diploid, the cells were subjected to metaphase mitotic arrest using Colcemide, then harvested by trypsin dispersal, hypotonic shock with 0.075 M KCl, fixation with 3:1 methanol/acetic acid fixative, and Giesmsa staining. Cell slide preparations were then analyzed for polyploidy.

Example 12

Calcium Imaging

To identify neurons physiologically, cells in selected plates were challenged with a depolarizing stimulus of 60 mM $K^+$, during which their cytosolic calcium levels were observed. Calcium imaging was performed using confocal microscopy of cultures loaded with fluo-3 acetoxymethyl-ester (fluo-3, Molecular Probes). An Olympus FluoView confocal scanning microscope, equipped with an argon laser and coupled to an Olympus IX70 microscope, was used to image the fluo-3 signal. A 3-fold calcium increase was required to depolarization for assigning neuronal identity.

Example 13

Telomerase Overexpression Immortalized Phenotypically-committed Progenitor Cells To assess the utility of telomerase overexpression as a means of immortalizing neural progenitor cells, freshly dissociated neuroepithelial progenitor cells were freshly transduced to constitutively express the hTERT gene. The fetal human spinal cord was chosen as a source of neural progenitors whose immortalization might be especially useful. Specifically, fresh dissociates of the spinal cord ventricular zone prepared from second trimester human fetuses were used. Samples were taken from 9, 11, 13, and 18 week spinal cords; each cord was divided into cervical, thoracic, and lumbar segments that were separately cultured. In addition, the 13 and 18 week cords were divided into ventral and caudal segments from which the spinal neuroepithelia were then dissected. (Keyoung et al., "Specific Identification, Selection and Extraction of Neural Stem Cells from the Fetal Human Brain," *Nature Biotechnology* 19:843–850 (2001), which is hereby incorporated by reference in its entirety). Within their first day in vitro, the spinal progenitor cells were infected with a VSVg-pseudotyped retrovirus encoding human telomerase reverse transcriptase (hTERT). This vector was established in pBABE-puro, with hTERT transcription placed under CMV control; this expression cassette was upstream to a puromycin resistance cassette, under IRES control. After expanding in bFGF-supplemented basal media for 1–2 weeks, the transduced cells were selected in 0.4 µg/ml puromycin for 2 weeks. Matched control cultures were infected with a retrovirus encoding pBABE-puro, without TERT. Positive selectants from both retroviral TERT and control infections were then subcloned and propagated in DMEM/F12/N1 with bFGF (10 ng/ml).

Successfully-selected human spinal cord lines were derived from all 4 time points sampled (9, 11, 13 and 18 wks g.a. from voluntary abortions). The 9 and 11 week spinal cord samples yielded 2 and 1 lines, respectively, while the 13 and 18 week spinal cord samples yielded one line each. For each hTERT overexpressing line that was generated, a corresponding control line of pBABE infected cells was also generated. Since the goal in this work was to use telomerase overexpression to immortalize phenotypically-restricted lines, those initial puromycin selectants that appeared to be multipotential, and hence possibly immortalized stem cells, were frozen for future study. Successfully-selected human spinal cord lines were derived from all 4 timepoints sampled (9, 11, 13 and 18 wks g.a.) (FIGS. 7A–I). The 9 and 11 week spinal cord samples yielded 3 lines that survived selection (2 and 1, respectively), while the 13 and 18 week samples yielded a single line each. Since the goal in this work was to use telomerase overexpression to immortalize phenotypically-restricted line, those initial puromycin selectants that appeared to be multipotential, and hence possibly immortalized stem cells, were frozen for future study. In this study, analysis has been restricted to one phenotypically-restricted lines, that after selection was noted to give rise only to neurons. This line, designated as hSC11-TERT, was the first line generated using this strategy. It was established from an 11 week ventral segment of the thoracolumbar spinal cord, that has been propagated continuously for 18 months. This line has now been propagated continuously for 23 months spanning >18 monthly passages, each of which included 7–10 cell divisions. Thus, it is estimated that this line has undergone at least 126 cell doublings, and perhaps as many as 180 (FIG. 6).

For each sample infected with hTERT, matched control cells were also infected with pBABE-puro only to control for the presence of the puromycin selection cassette. Those control cells that survived puromycin selection typically ceased expanding within the few weeks after antibiotic selection; no control lines survived beyond 10 months in vitro, or 55 estimated population doublings (PDs). Those that did appeared to be multipotential, in that they gave rise to both neurons and glia. These cells co-expressed nestin protein and the A2B5 epitope, suggesting that they represented neuroepithelial stem cells that might have continued to expand under these conditions regardless of TERT transduction. However, these lines slowly degraded over the ensuing months in vitro, such that by 3 months in culture, only mitotically inactive glial derivatives could be identified in these pBABE-puro-infected control lines. In contrast, their TERT-infected counterparts continued to expand thereafter in loosely-adherent neurospheres, without mitotic deceleration or phenotypic degradation (FIG. 6). Most importantly, many of the TERT-transduced lines were noted to generate only single morphologically-defined cell types, a phenotypic uniformity that was never observed in any of the control lines generated.

Example 15 hTERT-Transduced Spinal Progenitors Retained High-Level Telomerase Activity.

Figure 6:
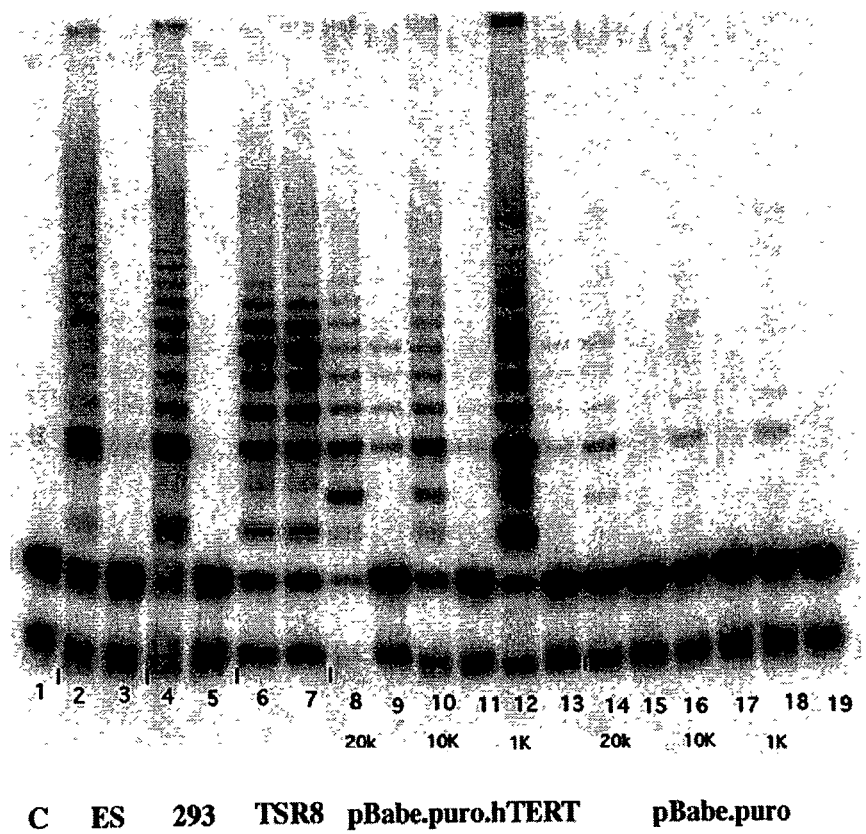
FIG. 6 shows that successfully-selected lines expressed high levels of telomerase activity. The telomeric repeat amplification protocol assay ("TRAP") revealed that retroviral-hTERT transduced cells expressed high levels of telomerase activity, whereas their matched controls did not. This is a typical TRAP gel for an hTERT-transduced cell line which shows the high telomerase activity of an hTERT-transfected human ventral spinal neuroepithelial culture. These cells were derived from 11 week gestational age cervical spinal cord and are the same line as shown in FIG. 5. Lane 1 is a cell-free negative control. Lanes 2 and 4 show human embryonic stem cells (2) and 293 cells (4), two positive control lines that express high levels of telomerase. High telomerase activity is indicated here by the ladder of bands 6 nucleotides apart, indicating hexameric nucleotide addition to the test substrate by cellular telomerase. Lanes 3 and 5 show inactivated extract negative controls. Lanes 6–7 show TSR8 (telomeric substrate, 8 repeats), a calibration standard for assessing the relative activity of the test cell lines. Lanes 8, 10, and 12 show test spinal neuronal progenitor cells, with 20,000, 10,000 and 1,000 extracted cells/lane. Telomerase activity was high over this entire range, a drop in TRAP activity as the cell number rose (compare lane 8 to 12) reflected competition of the target substrate for the labeled probe. When cell number was high, endogenous substrate levels were as well, resulting in competition for the labeled probe. Lanes 9, 11, and 13 show their negative controls. Lanes 14–19 show pBABE transfection controls. These cells were transfected with a control plasmid that expressed a puro selection cassette but which did not contain hTERT. They showed no measurable telomerase activity.
Figure 7:
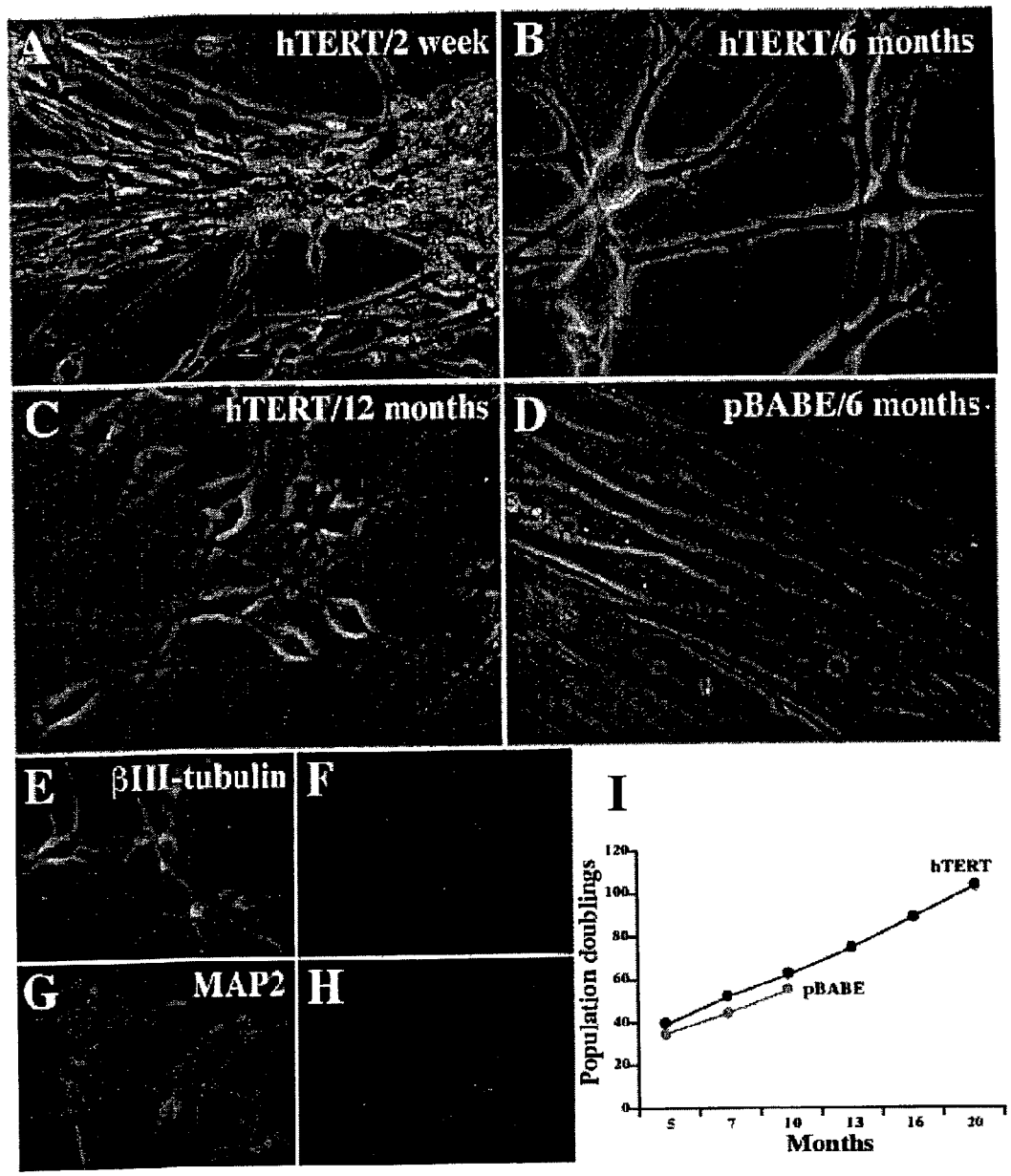
FIGS. 7A–I demonstrate that telomerase-immortalization of early spinal neuroepithelium yielded lines that included phenotypically-restricted neuronal progenitor cells. These images show hTERT-immortalized human spinal cord neuronal progenitor cells, designated hSC11V-TERT. This line was derived from human ventral spinal neuroepithelium, sampled from 11-week gestational age spinal cord.

Successfully-selected lines expressed varying but generally high levels of telomerase activity, as assessed by the telomeric repeat amplification protocol assay (TRAP) (FIG. 6). The telopmerase activity of hSC11V-TERT cells was estimated at approximately 55 PDs, and at a later time point corresponding to 125 PDs. pBABE-puro-trasduced control cells sampled after 45 PDs served as control. In the hSC11V-TERT cells, telomerase activity was observed at both time points (FIGS. 7A–I). In contrast, at 45 PDs the pBABE-puro-infected cells showed no telomerase activity; these data indicated that the prolonged and stable proliferative capacity of the hSC11-TERT line correlated with their overexpression of hTERT.

Example 16 hTERT Immortalized Dividing Progenitor Cells, but Did Not Render Mature Neurons Mitotic.

Figure 8:
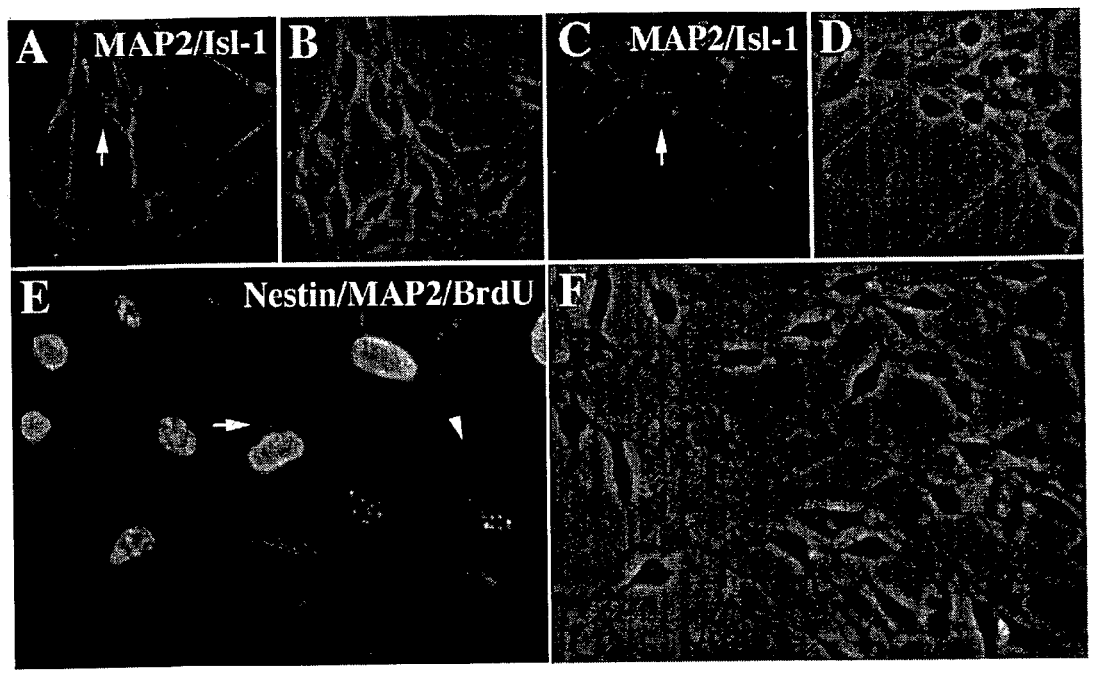
FIGS. 8A–F shows that telomerase-immortalized spinal progenitors can generate Islet1-defined motor neurons. The hSC11V-TERT line generated only neurons.

Cultures of telomerase-immortalized spinal neuronal progenitor cells retain mitotic competence, with persistent addition of new neurons to the cultures after as long as 8 months in vitro, spanning >60 cell doublings. It was asked which was the dividing phenotype—the hTERT-transduced neuron, its normally mitotic progenitor, or both? In other words, was neuronal addition to these cultures a result of the persistent division of hTERT-transduced neurons, or did it instead reflect only the division of an earlier neuronal progenitor phenotype. To address this issue, stable cultures of hTERT-transduced cell lines that generated antigenically-defined neurons were exposed to BrdU for just 6 hours, then fixed, immunolabeled for both precursor cells and mature neurons (using nestin and MAP-2 proteins), and then labeled for incorporated BrdU. This technique permitted the identification of dividing cells within each lineage. Among cutitured hSC-11V-TERT cells, it was found that whereas great numbers of BrdU$^+$ cells expressed nestin, none co-expressed MAP-2, a marker of mature neurons. To be sure, a great abundance of MAP2$^+$ neurons was noted in these cultures, but none of these incorporated BrdU. These results suggest that hTERT overexpression prolonged or immortalized the mitotic competence of progenitor cells but did not cause the aberrant division of mature neurons. Thus, the neurons arising from hTERT-immortalized progenitors did not themselves divide (FIG. 8). Rather, they were generated continuously from an hTERT-transduced mitotic progenitor that was itself enjoined from replicative senescence (FIG. 8).

Example 17

Phenotypically-Restricted Progenitors Were Immortalized as Such by hTERT Overexpression.

Figure 9:
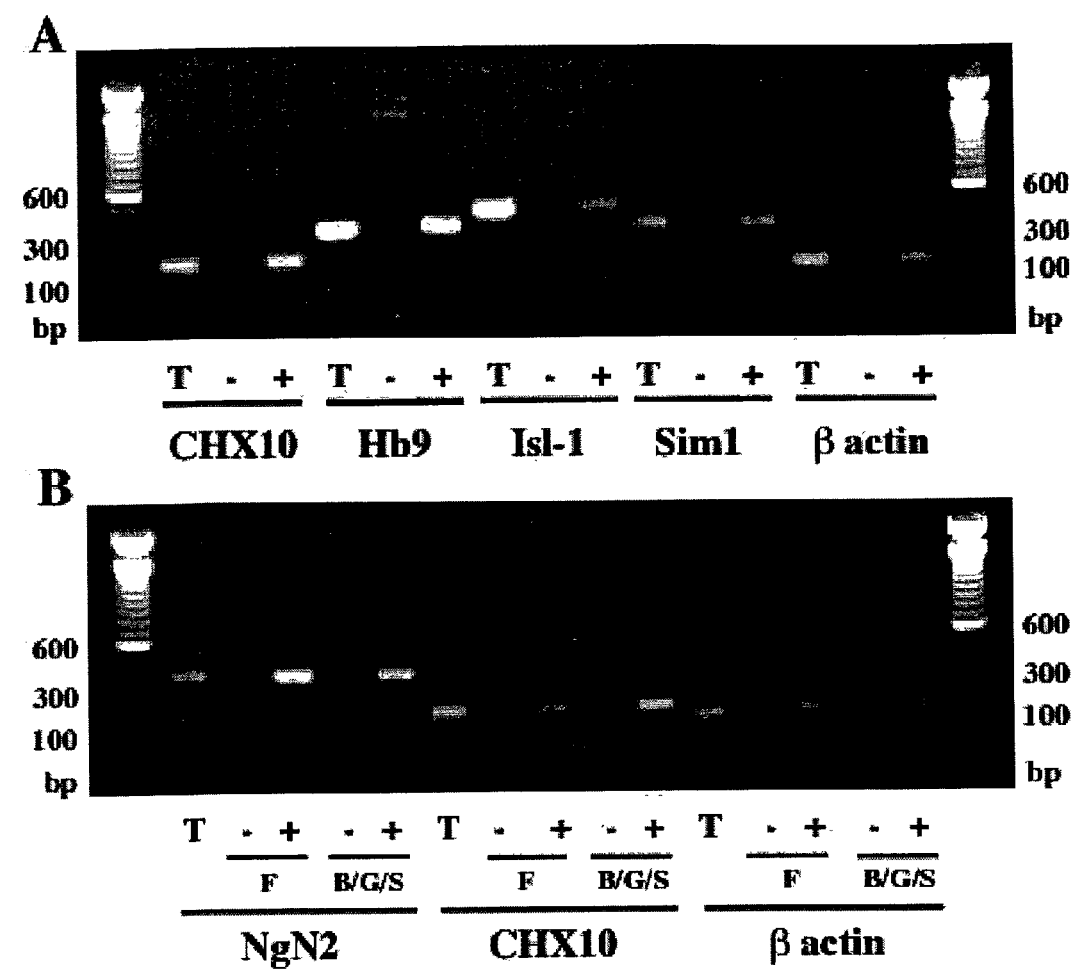
FIGS. 9A–B show that hSC11V-TERT cells express transcription factors specifying ventral spinal neurons.

The acquisition of neuronally-restricted progenitor lines such as hSC11V-TERT was to be expected from the 9 and 11 week g.a. samples, given the prevalence of neuronally-committed progenitor cells at these early gestational ages. Moreover, hSC11V-TERT cells remained true to the dorsoventral position from which the founder cells were derived. As such, this ventrally-derived spinal neuroepithelial line gave rise to a mixture of ventral neuronal phenotypes. These could be identified by a variety of permutations of the transcription factors chx10, sim1, Islet1 and Hb9. They included chx10$^+$ cells biased to generate V2 interneurons, sim1$^+$ cells that typically give rise to V3 neurons, and Islet1$^+$ and Hb9$^+$ cells, each of which can define motor neurons (FIG. 9). When cells from the hSC11-TERT line were induced to differentiate in the presence of BDNF/GDNF/serum for a short period of 4 days, a marked increase was observed in CHX10 expression compared to cells maintained in FGF, along with a smaller elevation in Hb9 mRNA. These were noted in tandem with a decreased expression of the βHLH transcription factor neurogenin-2, which was otherwise expressed in replicating hSC11V-TERT cells.

Example 18

Neurons Generated from hTERT-immortalized Progenitors Develop Mature Phenotypes

Figure 10:
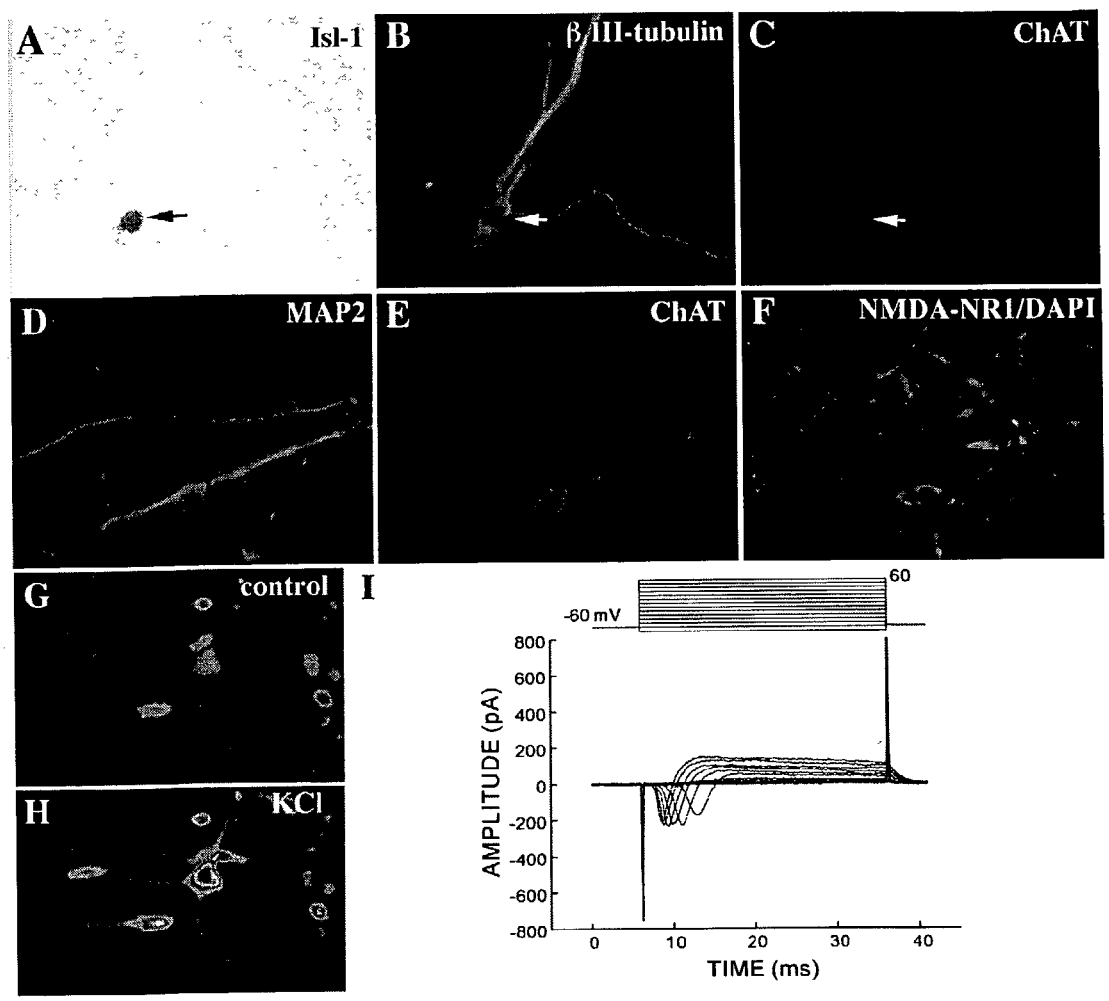
FIGS. 10A–I illustrate that hTERT-immortalized neuronal progenitors can generate functionally competent neurons.

In addition to their antigenic maturation, neurons generated by hSC11-TERT cells achieved functional competence. The Isl1$^+$ population expressed the NMDA-R1 glutamate receptor, as would be expected of both ventral interneurons and motor neurons, each of which receive glutamatergic input from descending corticospinal afferents. In addition, to establish the ability of neurons generated from hSCNP-TERT cells to respond in a neuronal fashion to depolarizing stimuli, selected cultures (n=4) were loaded with the calcium indicator dye fluo-3, and exposed to 60 mM K$^+$ during confocal microscopy. Some but not all hSCNP11-TERT cells displayed rapid, reversible, >4-fold elevations in cytosolic calcium in response to K$^+$, consistent with the activity of neuronal voltage-gated calcium channels (FIG. 10A).

These results suggest the acquisition of neuronal functional competence by neurons arising from hSC11-TERT cells. In addition, it was noted that the Islet1$^+$ neurons in these cultures expressed choline acetyl transferase, indicating their cholinergic phenotype. Islet1 is expressed by a number of neuronal phenotypes throughout the neuraxis. In the ventral segment of the cord, Islet1 is expressed by motor neurons, which can be defined antigenically by their co-expression of Islet 1 and ChAT (FIG. 10B). The co-expression of these two antigens by hSC11-TERT derived neurons suggested the in vitro production of motor neurons by these telomerase-immortalized spinal progenitor cells.

Example 19

Multiple Ventral Neuronal Phenotypes are Clonally-Derived

To determine whether the several phenotypes of neurons generated by these hTERT-immortalized progenitors were clonally-derived, Southern blotting of the hTERT insertion site was used to characterize the homogeneity—or lack thereof—of the insert sequence among cells within single cultures. Among those cultures examined (n=4; each of >$10^5$ cells), all harbored only single retroviral hTERT inserts, as manifested by a single band on Southern detection. Thus, clonal analysis suggested the co-derivation of several phenotypically-distinct but spatially contiguous neuronal phenotypes from single progenitor cells of the human spinal neuroepithelium.

Figure 11:
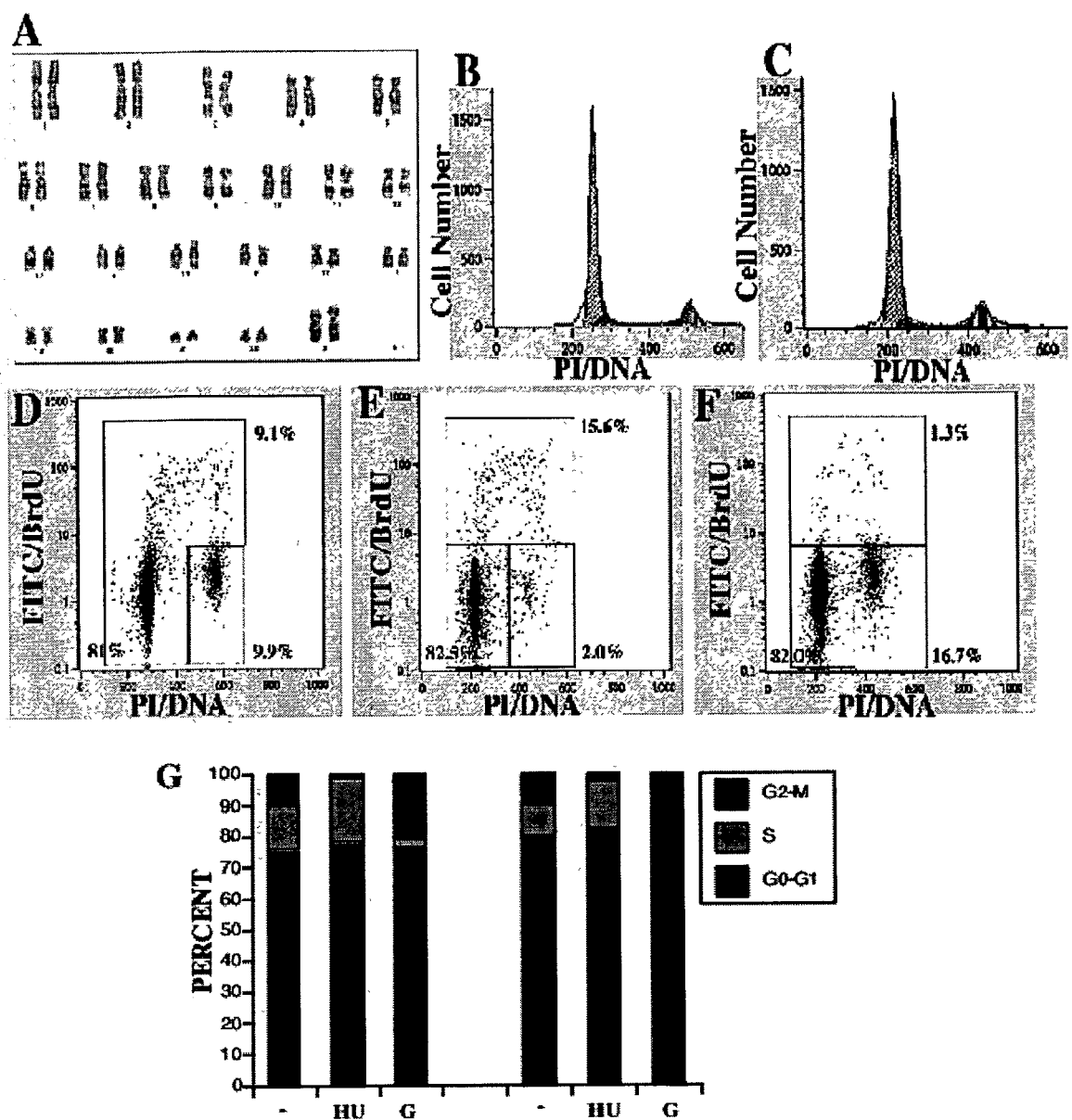
FIGS. 11A–G show that hSC11V-TERT cells retained karyotypic stability and cell cycle checkpoint integrity.

Example 20 hTERT-immortalized Progenitors Retain Both Euploidy and Karyotypic Normalcy with Passage As noted, telomerase overexpression is considered non-oncogenic in nature, and hTERT-transduction has not hitherto been associated with neoplastic transformation. Nonetheless, telomerase has been shown to affect myc transcriptional activation, and to, in turn, be upregulated by endogenous myc. As a result, hTERT overexpression does at least pose the theoretic risk of lowering cellular thresholds to anaplastic transformation.

hTERT-immortalized progenitors retained a normal chromosomal complement and karyotypes with extended passage in vitro (FIG. 11). In addition to karyotypic analysis, cell cycle analysis by flow cytometry was used to assess the DNA complement of hTERT-immortalized cells after passage 13 and 30, which correspond roughly to the $55^{th}$ and $120^{th}$ doublings. Prior to fixation for cell cycle analysis, the cells were exposed to biomodeotyuride for 6 hours to label the S-phase mitotic neural progenitors, it was found that the overwhelming majority of cells were diploid, with no evidence of hyperploidization at either passage, and with no increment in non-euploidy during progression from 55 to the $120^{th}$ passage (FIG. 11).

In addition, cell cycle progression was blocked to assess the stability of hSC-11V-TERT's major cell cycle check points. For this purpose, hydroxyurea, which induces a p-53 independent S-phase arrest, and gamma-irradiation, which induces a p-53 dependent G1 cell arrest, were separately used. Both effectively blocked cell cycle progression. The cells responded appropriately to hydroxyurea and gamma-irradiation by showing an increase in the percentage of cells in the S-phase, and a concurrent increase in the G1/S ratio (FIG. 11). Thus, hSC-11V-TERT cells obeyed major cell cycle check-points. They exhibited neither evidence of hyperploidization at either passage, nor any increment in non-euploidy during progression from 55 to the $120^{th}$ passage (FIG. 11). These data suggest that hSC-11V-TERT cells are neither aneuploid nor anaplastic.

Telomerase overexpression permits the generation of stable immortalized lines of human neuronal or glial progenitor cells, whose progeny were able to differentiate as mature cells of relatively restricted and uniform phenotypes. These hTERT-immortalized cell lines survived puromycin selection, were mitotically responsive to FGF2, maintained high levels of telomerase activity, and remained both phenotypically- and karyotypically-stable beyond 120 divisions in vitro. These lines included restricted lineages that gave rise to either neurons or glia but not both, reminiscent of primary progenitor cells from which v-myc immortalized lines have been established. Unlike such v-myc transformants, however, the TERT-immortalized progenitors were non-anaplastic and non-oncogenic, and generated phenotypically-restricted progeny that were capable of normal antigenic and physiologic maturation. One prototypic hTERT-immortalized neuronal progenitor line, derived from a telomerase-transduced 11 week ventral spinal cord, has now been passaged for 18 months, with at least 126 cell doublings that have generated a limited and repertoire of well-defined ventral spinal neuronal subtypes. This line was typical of the neuronal progenitor lines generated through hTERT-immortalization, which were typically regionally-defined as well as phenotypically-restricted. Given their extraordinary expansion capacity, phenotypic stability and unceasing mitotic activity, these lines allowed the prolific generation of relatively uniform populations of human spinal neurons.

The advent of preparations of neural progenitor and stem cells has led to a number of studies that have investigated their use in injury and disease, typically following their direct implantation into an injury site. Yet these initial studies have shared a number of features that have limited their likely clinical utility. In particular, studies have been conducted with little or no regard to the region of ventricular zone from which they are derived, and whether that sampled region typically generates the types of neurons and glia that are required for the intended treatment. For instance, spinal cord repair may require spinal cord rather than brain-derived cells, because brain progenitors may be specified to quite different phenotypes, both in terms of homeodomain code-dependent positional cues and transmitter repertoires, than progenitors derived from spinal cord regions.

Such positionally-defined progenitors may be harvested simply by extracting them from tissue at the desired stage and location at which a desired phenotype is generated. But although stem cells derived from given regions of the neuroepithelium may give rise to neuronal and glial phenotypes characteristic of that region, more-restricted progenitor cell types, such as those giving rise only to midbrain neurons, are capable of too little expansion to be useful. As a result, the field has lacked a means of immortalizing, in a non-oncogenic fashion, phenotypically-restricted cell types of a given fate, such a spinal cord motor neuronal progenitors. In response to this need, a means of immortalizing cells with hTERT has been established, to yield mitotically active but non-transformed cell lines, whose progeny reliably and reproducibly give rise to cells true to the phenotype of their transduced parental progenitor.

In this regard, it is worth noting that specific types of neural progenitor cells may now be prospectively identified and specifically extracted from larger populations, by fluorescence-activated sorting (FACS) of cells transfected with plasmids bearing GFPs driven by cell-specific promoters (Wang et al., "Isolation of Neuronal Precursors by Sorting Embryonic Forebrain Transfected with GFP Regulated by the T alpha 1 Tubulin Promoter," *Nature Biotechnol* 16:196–201 (1998), which is hereby incorporated by reference in its entirety]. This technique has permitted the selective extraction of neuronal progenitor cells, multipotential stem cells, hippocampal progenitors, and glial progenitors, from both the fetal and adult human brain (Roy et al., "Identification, Isolation, and Promoter-defined Separation of Mitotic Oligodendrocyte Progenitor Cells from the Adult Human Subcortical White Matter," *J Neurosci* 19:9986–95 (1999); Roy et al., "In vitro Neurogenesis by Progenitor Cells Isolated from the Adult Human Hippocampus," *Nat Med* 6:271–7 (2000); and Keyoung et al., "Specific Identification, Selection and Extraction of Neural Stem Cells from the Fetal Human Brain," *Nature Biotechnology* 19:843–850 (2001), which are hereby incorporated by reference in their entirety). On this basis, hTERT can now be overexpressed in FACS-sorted, phenotypically-defined populations of human neural precursor cells. This approach may allow not only the establishment of hTERT-immortalized lines of phenotypically-restricted human neural progenitors, but to do so using preselected phenotypes, selected and then immortalized on the basis of their commitment to pre-defined lineages and functional capabilities. Using the approach described here, immortalized lines of phenotypically-restricted human progenitor cells, each with a pre-defined functional repetoire and positional origin, may now be derived. By virtue of the phenotypic stability and maturation competence of the progeny generated by hTERT-immortalized progenitors, such "made to order" immortalized progenitor lines, prepared from promoter-defined, FACS-sorted human progenitors, may prove particularly useful vectors for cell-based neurological therapy.

Together, these results indicate that hTERT overexpression permits the generation of stable lines of lineage-restricted human neural progenitor cells. hTERT overexpression appears sufficient to support the persistent mitotic competence of lineage-restricted neuronal and glial progenitor cells, hence opening the possibility for propagating progenitors restricted to given lineages and positionally-defined phenotypes, such as ventral neurons. Further refinement may permit the generation of yet more specified lines, such as those able to produce only motor neurons, or only neurons of a given transmitter type. The potential of such cell lines to provide the substrates for the rational structural restoration of the damaged spinal cord may be profound.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method of immortalizing neural progenitor cells comprising:
   providing a population of neural progenitor cells and
   immortalizing the population of neural progenitor cells by introduction of a nucleic acid sequence encoding telomerase reverse transcriptase operably linked to a promoter, either before or after the neural progenitor cells are enriched or purified wherein said telomerase reverse transcriptase is produced in sufficient quantity to immortalize said neural progenitor cells.

2. The method of claim 1, wherein the immortalized neural progenitor cells give rise to lineage-restricted neural progenitor cells and their progeny.

3. The method of claim 1, wherein said immortalizing is carried out by transducing the enriched or purified population of neural progenitor cells.

4. The method of claim 3, wherein the enriched or purified population of neural progenitor cells are transduced by viral-mediated transduction.

5. The method of claim 4, wherein said viral-mediated transduction is selected from the group consisting of adenovirus-mediated transduction, retrovirus-mediated transduction, adeno-associated virus-mediated transduction, lentivirus-mediated transduction, and herpesvirus-mediated transduction.

6. The method of claim 5, wherein said viral-mediated transduction is retrovirus-mediated transduction.

7. The method of claim 5, wherein said viral-mediated transduction is adenovirus-mediated transduction.

8. The method of claim 5, wherein said viral-mediated transduction is adeno-associated virus-mediated transduction.

9. The method of claim 5, wherein said viral-mediated transduction is lentivirus-mediated transduction.

10. The method of claim 5, wherein said viral-mediated transduction is herpesvirus-mediated transduction.

11. The method of claim 3, wherein the enriched or purified population of neural progenitor cells are transduced by electroporation.

12. The method of claim 3, wherein the enriched or purified population of neural progenitor cells are transduced by biolistic transduction.

13. The method of claim 3, wherein the enriched or purified population of neural progenitor cells are transduced by liposomal-mediated transduction.

14. The method of claim 1, wherein said immortalizing is carried out by transducing the enriched or purified population of neural progenitor cells with a vector encoding a telomerase reverse transcriptase.

15. The method of claim 14, wherein the enriched or purified population of neural progenitor cells is lineage-restricted.

16. The method of claim 1, wherein the neural progenitor cells are selected from the group consisting of neuronal progenitor cells, oligodendrocyte progenitor cells, hippocampal progenitor cells, and neural stem cells.

17. The method of claim 1, wherein the neural progenitor cells are selected from dopaminergic progenitor cells, cholinergic progenitor cells, motor neuronal progenitor cells, dorsal neuronal progenitor cells, ventrally-derived neuronal progenitor cells, ventral motor neuronal progenitor cells, ventral mesencephalic neuronal progenitor cells, and mesencephalic dopaminergic progenitor cells.

18. The method of claim 1, wherein the neural progenitor cells are from the spinal cord.

19. The method of claim 1, wherein the neural progenitor cells are from the brain.

20. The method of claim 19, wherein the neural progenitor cells are from the forebrain, hypothalamus, midbrain, pons, or medulla.

21. The method of claim 1, wherein the neural progenitor cells are from the pancreatic islet.

22. The method of claim 1, wherein the neural progenitor cells are from the retina.

23. The method of claim 1, wherein the neural progenitor cells are from a human.

24. The method of claim 23, wherein the neural progenitor cells are from an adult.

25. The method of claim 23, wherein the neural progenitor cells are of fetal origin.

26. The method of claim 1, wherein said providing an enriched or purified population of neural progenitor cells comprises:
   providing a mixed population of cell types which population includes neural progenitor cells;
   selecting a promoter which functions in said neural progenitor cells;
   introducing a nucleic acid molecule encoding a marker protein under control of said promoter into the mixed population of progenitor cells;
   allowing the population of progenitor cells to express the marker protein; and
   separating the cells expressing the marker protein from the mixed population of cells, wherein said separated cells are neural progenitor cells.

27. The method of claim 26, wherein the marker protein is a fluorescent protein.

28. The method of claim 26, wherein the promoter is selected from the group consisting of a MAP-1B promoter, an NCAM promoter, an HES-5HLH protein promoter, an α1-tubulin promoter, an α-internexin promoter, a GAP-43 promoter, a JC virus minimal core promoter, a cyclic nucleotide phosphorylase II promoter, a nestin enhancer, and musashi promoter.

29. The method of claim 26, wherein the promoter is selected from the group consisting of a tyrosine hydroxylase promoter, a choline acetyltransferase promoter, a glutamic acid decarboxylase promoter, an MNR2 gene promoter, an Hb9 gene promoter, a sox2 homeodomain gene promoter, a bHLH protein promoter, a neurogenin-2 promoter, a NKx2.2 promoter, and an olig2 promoter.

30. The method according to claim 1, wherein said providing an enriched or purified population of neural progenitor cells comprises:
providing a mixed population of cell types which population includes neural progenitor cells and
separating the enriched or purified population of neural progenitor cells from the mixed population using surface marker protein specific to and naturally present in the enriched or purified population of neural progenitor cells.

31. The method according to claim 30, wherein the surface marker protein is selected from the group consisting of A2B5 and A133.

32. The method according to claim 1, wherein said immortalizing is carried out before the neural progenitor cells are enriched or purified.

33. The method according to claim 1, wherein said immortalizing is carried out after the neural progenitor cells are enriched or purified.

34. An enriched or purified population of immortalized neural progenitor cells comprising a nucleic acid sequence encoding telomerase reverse transcriptase operably linked to a heterologous promoter, wherein said telomerase reverse transcriptase is produced in sufficient quantity to immortalize said neural progenitor cells.

35. The enriched or purified population of claim 34, wherein the progenitor cells are neural progenitor cells.

36. The enriched or purified population of claim 35, wherein the neural progenitor cells are selected from the group consisting of neuronal progenitor cells, oligodendrocyte progenitor cells, hippocampal progenitor cells, and neural stem cells.

37. The enriched or purified population of claim 35, wherein the neural progenitor cells are from the spinal cord.

38. The enriched or purified population of claim 35, wherein the neural progenitor cells are from the brain.

39. The enriched or purified population of claim 38, wherein the neural progenitor cells are from forebrain, hypothalamus, midbrain, pons, or medulla.

40. The enriched or purified population of claim 35, wherein the neural progenitor cells are from the pancreatic islet.

41. The enriched or purified population of claim 35, wherein the neural progenitor cells are from the retina.

42. The enriched or purified population of claim 35, wherein the neural progenitor cells are from a human.

43. The enriched or purified population of claim 42, wherein the neural progenitor cells are from an adult.

44. The enriched or purified population of claim 42, wherein the neural progenitor cells are of fetal origin.

45. The enriched or purified population of claim 34, wherein the neural progenitor cells lack significant endogenous telomerase activity.

* * * * *